US011950868B2

(12) United States Patent
Hung et al.

(10) Patent No.: US 11,950,868 B2
(45) Date of Patent: Apr. 9, 2024

(54) SYSTEMS AND METHODS FOR SELF-ALIGNMENT AND ADJUSTMENT OF ROBOTIC ENDOSCOPE

(71) Applicant: Noah Medical Corporation, San Carlos, CA (US)

(72) Inventors: Carol Kayee Hung, Palo Alto, CA (US); Piotr Robert Slawinski, Sunnyvale, CA (US); Hendrik Thompson, San Francisco, CA (US); Maziyar Keshtgar, San Bruno, CA (US)

(73) Assignee: Noah Medical Corporation, San Carlos, CA (US)

( * ) Notice: Subject to any disclaimer, the term of this patent is extended or adjusted under 35 U.S.C. 154(b) by 0 days.

(21) Appl. No.: 18/466,010

(22) Filed: Sep. 13, 2023

(65) Prior Publication Data
US 2024/0016557 A1    Jan. 18, 2024

Related U.S. Application Data

(63) Continuation of application No. PCT/US2023/023139, filed on May 22, 2023.
(Continued)

(51) Int. Cl.
*A61B 34/32* (2016.01)
*A61B 34/10* (2016.01)
(Continued)

(52) U.S. Cl.
CPC .............. *A61B 34/32* (2016.02); *A61B 34/10* (2016.02); *A61B 34/20* (2016.02);
(Continued)

(58) Field of Classification Search
CPC ......... A61B 34/32; A61B 34/10; A61B 34/20; A61B 2034/107; A61B 2034/2051; A61B 2034/2055; A61B 2034/301
See application file for complete search history.

(56) References Cited

U.S. PATENT DOCUMENTS

| 9,492,235 B2 | 11/2016 | Hourtash et al. |
| 2017/0172382 A1 | 6/2017 | Nir et al. |
| (Continued) | | |

FOREIGN PATENT DOCUMENTS

| WO | 2021146339 A1 | 7/2021 |
| WO | WO-2023230013 A1 | 11/2023 |

OTHER PUBLICATIONS

PCT/US2023/023139 International Search Report and Written Opinion dated Aug. 14, 2023.

*Primary Examiner* — Basil T. Jos
(74) *Attorney, Agent, or Firm* — Wilson Sonsini Goodrich & Rosati

(57) ABSTRACT

A method is provided for a robotic endoscope system. The method comprises: generating a 3D depth map of an environment surrounding the robotic endoscope system; autonomously actuating a self-propelled base of a robotic support system to a desired location relative to a patient bed based on the 3D depth map, wherein the robotic support system comprises a robotic arm coupled to the self-propelled base at a proximal end and coupled to a flexible endoscope apparatus via an instrument driving mechanism (IDM) at a distal end; and actuating the robotic arm to align the IDM to a component coupled to or part of the patient bed.

26 Claims, 20 Drawing Sheets

Related U.S. Application Data

(60) Provisional application No. 63/347,179, filed on May 31, 2022, provisional application No. 63/345,287, filed on May 24, 2022.

(51) Int. Cl.
*A61B 34/20* (2016.01)
*A61B 34/30* (2016.01)

(52) U.S. Cl.
CPC . *A61B 2034/107* (2016.02); *A61B 2034/2051* (2016.02); *A61B 2034/2055* (2016.02); *A61B 2034/301* (2016.02)

(56) References Cited

U.S. PATENT DOCUMENTS

2021/0049762 A1    2/2021   Mintz et al.
2023/0380659 A1*   11/2023   Refai .................. H04N 13/254

* cited by examiner

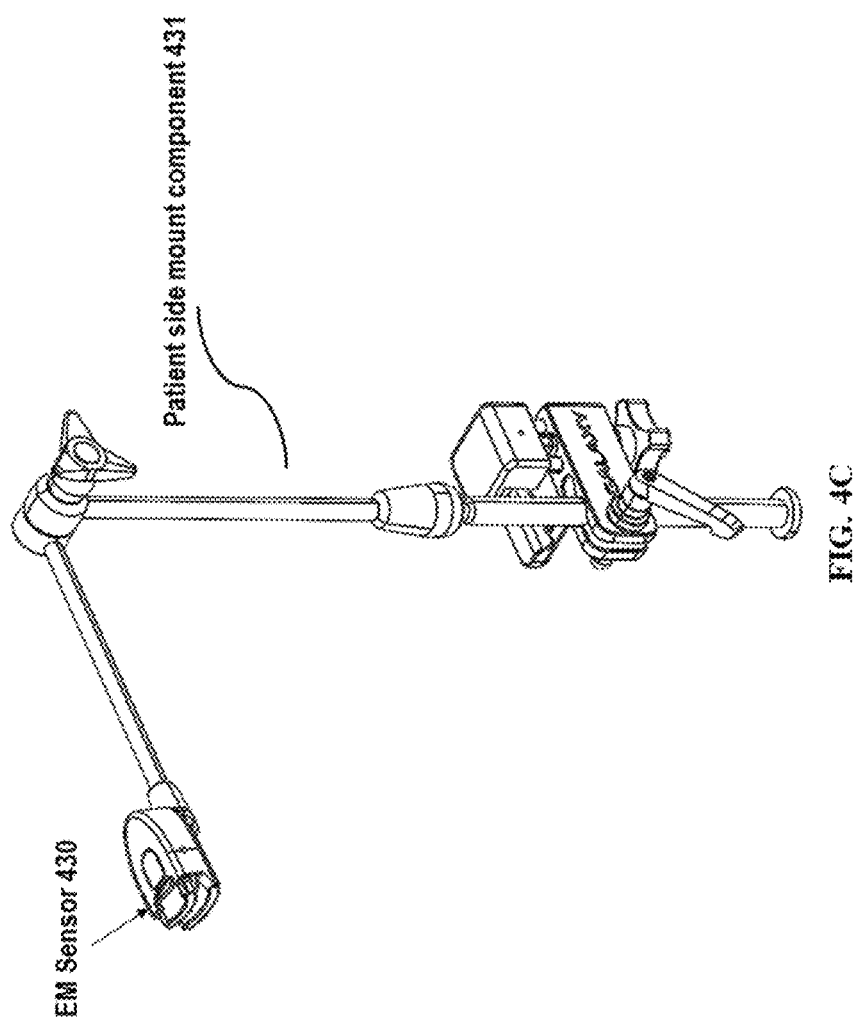

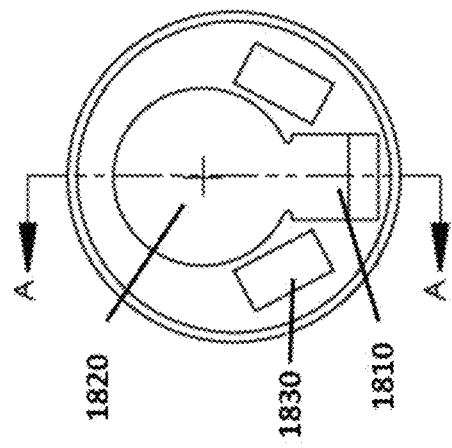
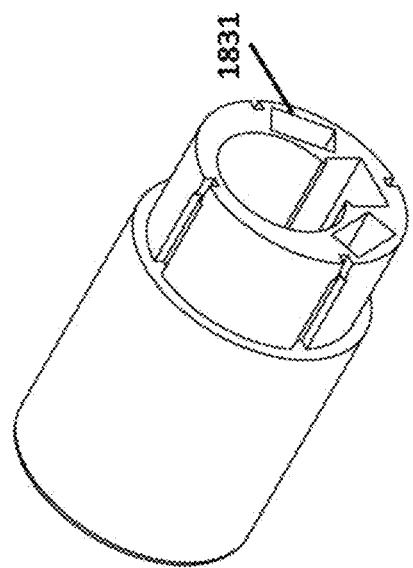
FIG. 18

SYSTEMS AND METHODS FOR SELF-ALIGNMENT AND ADJUSTMENT OF ROBOTIC ENDOSCOPE

CROSS-REFERENCE

This application is a continuation of International Patent Application No. PCT/US2023/023139, filed May 22, 2023, which claims priority to U.S. Provisional Patent Application No. 63/345,287, filed on May 24, 2022, and U.S. Provisional Patent Application No. 63/347,179, filed on May 31, 2022, each of which is entirely incorporated herein by reference.

BACKGROUND OF THE INVENTION

Endoscopy procedures use an endoscope to examine the interior of a hollow organ or cavity of the body. Unlike many other medical imaging techniques, endoscopes are inserted into the organ directly. Flexible endoscope that can deliver instinctive steering and control is useful in diagnosing and treating diseases that are accessible through any natural orifice in the body. Depending on the clinical indication, the endoscope may be designated as bronchoscope, ureteroscope, colonoscope, gastroscope, ENT scope, and various others. For example, flexible bronchoscope may be used for lung cancer diagnosis and/or surgical treatment. However, one challenge in bronchoscopy is reaching the upper lobe of the lung while navigating through the airways. In another example, flexible endoscopy has been used to inspect and treat disorders of the gastrointestinal (GI) tract without the need for creating an opening on the patient's body. The endoscope is introduced via the mouth or anus into the upper or lower GI tracts respectively. A miniature camera at the distal end captures images of the GI wall that help the clinician in their diagnosis of the GI diseases. Simple surgical procedures (like polypectomy and biopsy) can be performed by introducing a flexible tool via a working channel to reach the site of interest at the distal end.

Endoscopes are traditionally made to be re-usable, which may require thorough cleaning, dis-infection, and/or sterilization after each procedure. In most cases, cleaning, dis-infection, and sterilization may be aggressive processes to kill germs and/or bacteria. Such procedures may also be harsh on the endoscopes themselves. Therefore, the designs of such re-usable endoscopes can often be complicated, especially to ensure that the endoscopes can survive such harsh cleaning, dis-infection, and sterilization protocols. Periodical maintenance and repairs for such re-usable endoscopes may often be needed.

Low cost, disposable medical devices designated for a single-use have become popular for instruments that are difficult to clean properly. Single-use, disposable devices may be packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. Traditional endoscopes often include a handle that operators use to maneuver the endoscope. For single-use endoscopes, the handle usually encloses the camera, expensive electronics, and mechanical structures at proximal end in order to transmit the video and allow the users to maneuver the endoscope via a user interface. This may lead to high cost of the handle for a single-use endoscope.

The process for setting up of medical robots can be time-consuming and challenging due to the number of accessories to set up and the complex workflows. The setup times can result in longer room turnover time, causing procedural delays. Examples of the challenging steps of the current system workflow are: (1) positioning the robotic system in a location that is appropriate for the procedure and (2) aligning the instrument drive mechanism to the patient side. These steps are challenging because the user has to consider the placement of other equipment in the room that is needed for the procedure and gain spatial understanding of the workspace of the robotic components while manually performing these steps. During the procedure, if there are any changes to the setup of the room, the user has to manually make adjustments to the system to accommodate.

SUMMARY OF THE INVENTION

Recognized herein is a need for a robotic endoscopic platform or system that allows for autonomous self-adjustment of the robotic endoscopic system in response to real-time operating environment. The present disclosure addresses the above need by providing methods and systems capable of detecting and tracking the system's operating environment (e.g., external environment surrounding the system) and automatically making adjustments to the system thereby (1) simplifying the workflow for an operator during system setup and/or during the procedure and (2) enabling system configurations that are more optimal than placements completed manually which may be deemed acceptable but non-optimal. In some embodiments, the autonomous processes and/or movement of the system may comprise alignment of an instrument drive mechanism (IDM) of the robotic endoscopic device to a patient-side mount, alignment of the robotic base station (e.g., robotic cart) relative to the patient or hospital suite equipment, recognition of other technologies/equipment and auto-configuration for compatibility, collision avoidance between the system and patient and/or other objects in the operating environment, self-adjusting the robotic arm or IDM based on real-time instrument buckling detection and monitoring of breathing/vitals of the patient, etc.

In an aspect of the present disclosure, a method is provided for a robotic endoscope system. The method comprises: generating a 3D depth map of an environment surrounding the robotic endoscope system; autonomously actuating a self-propelled base of a robotic support system to a desired location relative to a patient bed based on the 3D depth map, where the robotic support system comprises a robotic arm coupled to the self-propelled base at a proximal end and coupled to a flexible endoscope apparatus via an instrument driving mechanism (IDM) at a distal end; autonomously actuating arm for collision avoidance; and actuating the robotic arm to align the IDM to a component coupled to or part of the patient bed. The methods implemented for enabling autonomous repositioning of system components given 3D depth map inputs require algorithms for processing and filtering the image data, mapping image data to inputs for the robotics control algorithms, and algorithms for obstacle voidance.

Recognized also herein are devices and systems comprising endoscopes which may be disposable and may not require extensive cleaning procedures. The present disclosure provides low-cost, single-use articulatable endoscope for diagnosis and treatment in various applications such as bronchoscopy, urology, gynecology, arthroscopy, orthopedics, ENT, gastro-intestine endoscopy, neurosurgery, and various others. In some embodiments, the present disclosure provides a single-use, disposable, robotically controlled bronchoscope for use with a robotic system to enable diagnostic evaluation of lesions anywhere in the pulmonary anatomy. It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

It should be noted that the provided autonomous configuration, alignment and collision avoidance methods, endoscope components and various components of the device can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

In an aspect, a method is provided for controlling a robotic endoscope system moving and operating in an environment. The method comprises: generating a 3D depth map of an environment surrounding the robotic endoscope system; autonomously actuating a self-propelled base of a robotic support system to a desired location relative to a patient bed based on the 3D depth map, where the robotic support system comprises a robotic arm coupled to the self-propelled base at a proximal end and an instrument driving mechanism (IDM) at a distal end; and actuating the robotic arm to autonomously align the IDM to a component coupled to or as a part of the patient bed.

In a related yet separate aspect, a system is provided for controlling a robotic endoscope system The system comprises: a memory storing computer-executable instructions; one or more processors in communication with the robotic endoscope system and configured to execute the computer-executable instructions to: generate a 3D depth map of an environment surrounding the robotic endoscope system; autonomously actuate a self-propelled base of a robotic support system to a desired location relative to a patient bed based on the 3D depth map, wherein the robotic support system comprises a robotic arm coupled to the self-propelled base at a proximal end and an instrument driving mechanism (IDM) at a distal end; and actuate the robotic arm to autonomously align the IDM to a component coupled to or as a part of the patient bed.

In some embodiments, the 3D depth map is generated based at least in part on 3D point cloud data. in some cases, the method further comprises processing the 3D depth map to detect the patient bed and computing a position and orientation of the robotic support system relative to the patient bed. In some embodiments, a flexible endoscope apparatus is releasably coupled to the IDM after the IDM is aligned to the component coupled to or as a part of the patient bed.

In some embodiments, the method further comprises controlling a movement of the robotic arm to move the IDM to a predetermined distance from the component coupled to or as a part of the patient bed. In some cases, the method further comprises loading a flexible endoscope apparatus to be coupled to the IDM at a proximal end and coupled to the component at a distal end. In some cases, the method further comprises automatically adjusting a position of the IDM relative to the component upon detection of a buckling event.

In some embodiments, the method further comprises detecting and recognizing an object in the environment and reconfiguring the robotic arm to avoid collision with the object while maintaining a position and orientation of the IDM. In some cases, the method further comprises detecting a buckling of a flexible catheter coupled to the IDM while the flexible catheter is inserted into a body of a patient. In some instances, the method further comprises executing a responsive velocity control algorithm to control a velocity of the tip of the flexible catheter while reconfiguring the robotic arm to avoid collision with the object.

In some embodiments, the IDM is autonomously aligned to the component based at least in part on sensor data. In some cases, the sensor data is captured by electromagnetic sensors. In some cases, the sensor data is captured by a camera including a fiducial marker placed on the component and the 3D depth map comprises at least a 3D location of the fiducial marker.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 4B and 4C shows an example of auto-alignment of IDM (instrument drive mechanism) based on EM sensor data.

FIG. 11 shows an example of a robotic bronchoscope comprising a handle portion and a flexible elongate member.

FIG. 12 shows an example of an instrument driving mechanism providing mechanical interface to the handle portion of the robotic bronchoscope.

FIG. 18 shows an example distal portion of the catheter with integrated imaging device and the illumination device.

DETAILED DESCRIPTION OF THE INVENTION

Figure 1:
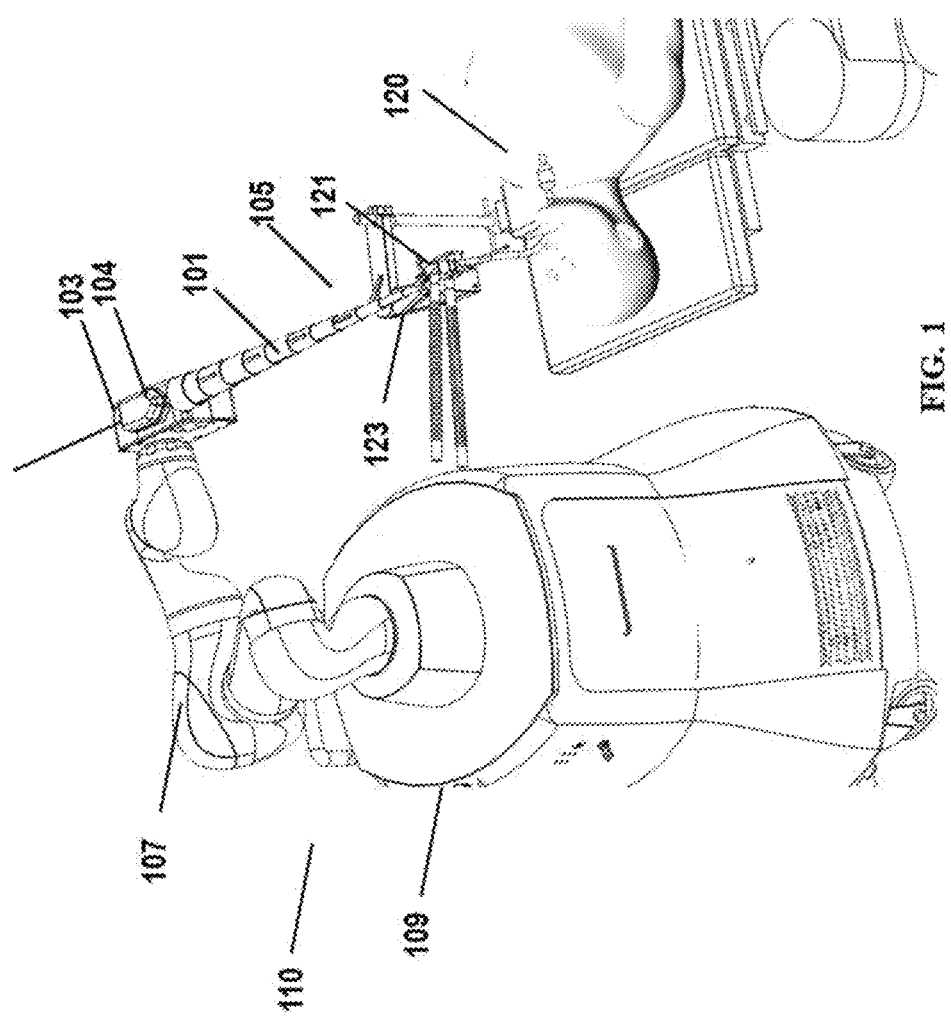
FIG. 1 schematically shows a robotic platform, in accordance with some embodiments of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

While exemplary embodiments will be primarily directed at a device or system for bronchoscopy, one of skill in the art will appreciate that this is not intended to be limiting, and the devices described herein may be used for other therapeutic or diagnostic procedures and in various anatomical regions of a patient's body. The provided device or system can be utilized in urology, gynecology, rhinology, otology, laryngoscopy, gastroenterology with the endoscopes, combined devices including endoscope and instruments, endoscopes with localization functions, one of skill in the art will appreciate that this is not intended to be limiting, and the devices described herein may be used for other therapeutic or diagnostic procedures and in other anatomical regions of a patient's body, such as such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat, and various others, in the forms of: NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, Orthopedic Endoscopes, and others, in combination with various tools or instruments.

The systems and apparatuses herein can be combined in one or more of many ways to provide improved diagnosis and therapy to a patient. Systems and apparatuses provided herein can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms distal and proximal may generally refer to locations referenced from the apparatus, and can be opposite of anatomical references. For example, a distal location of a primary shaft or catheter may correspond to a proximal location of an elongate member of the patient, and a proximal location of the primary sheath or catheter may correspond to a distal location of the elongate member of the patient.

As described above, setting up a robotic endoscopic system can be time consuming and challenging due to the complexity of the operating environment, requirement for accurate alignment between the instrument and patient body part and various other reasons. The present disclosure provides methods and systems capable of detecting and tracking the system's operating environment and automatically making adjustments to the system thereby simplifying the workflow during system setup and/or during the procedure. In some embodiments, the autonomous processes and/or movement of the system may comprise alignment of an instrument drive mechanism (IDM) of the robotic endoscopic device to a patient-side mount, alignment of the robotic base (robot cart) relative to the patient or hospital suite equipment, recognition of other technologies/equipment and auto-configuration for compatibility, collision avoidance between the system and patient and/or other objects in the operating environment, self-adjusting the robotic arm or IDM based on real-time instrument buckling detection and monitoring of breathing/vitals of the patient, and other functions as described elsewhere herein.

The operating environment of the robotic endoscope system may comprise one or more objects. The robotic endoscope system may be capable of detecting the one or more objects in the operating environment, generating a 3D map with depth information, performing autonomous alignment of the instrument drive mechanism with respect to the patient bed or body part, and self-adjusting its placement and configuration to avoid collision with the one or more objects. The one or more objects may comprise, for example, system accessories (e.g., system monitor, a monitor pole), external monitors, patient bed, patient, imaging equipment (e.g., fluoroscopy c-arm), anesthesia cart and other equipment or subject (e.g., operator, surgeon) in the operating environment before or during surgical operation.

FIG. 1 schematically shows a robotic platform 100. The platform may comprise a robotic endoscope system including one or more flexible articulatable surgical instruments 105, and a support apparatus 110 such as a robotic manipulator (e.g., robotic arm) to drive, support, position or control the movements and/or operation of the robotic system. The robotic platform may further include peripheral devices and subsystems such as imaging systems that may assist and/or facilitate the navigation of the elongate member to the target site in the body of a subject 120.

The robotic endoscope system is provided for performing surgical operations or diagnosis with improved performance at low cost. For example, the robotic endoscope system may comprise a steerable catheter that can be entirely disposable. As shown in FIG. 1, the robotic endoscope system may comprise a steerable catheter assembly 105 and a robotic support system 110, for supporting or carrying the steerable catheter assembly. The steerable catheter assembly can be an endoscope. In some embodiments, the steerable catheter assembly may be a single-use robotic endoscope. In some embodiments, the robotic endoscope system may comprise an instrument driving mechanism (IDM) 103 that is attached to the distal end of the robotic arm 107 of the robotic support system. The instrument driving mechanism may be provided by any suitable controller device (e.g., hand-held controller) that may or may not include a robotic system. The instrument driving mechanism may provide mechanical and electrical interface to the steerable catheter assembly 105. The mechanical interface may allow the steerable catheter assembly 105 to be releasably coupled to the instrument driving mechanism 103. For instance, a handle portion 104 of the steerable catheter assembly can be attached to the instrument driving mechanism (IDM) via quick install/release means, such as magnets, spring-loaded levels and the like. In some cases, the steerable catheter assembly may be coupled to or released from the instrument driving mechanism manually without using a tool. The instrument driving mechanism may be used to control the elongate member or robotic catheter assembly in two or more degrees of freedom (e.g., articulation).

The robotic support system 110 may comprise a robotic arm 107 and a mobile base (e.g., robotic cart) 109. The robotic arm 107 may initiate the positioning of the robotic catheter assembly or other robotic instrument. In some cases, a user interface, robotic control modules, and the robotic arm may be mounted to the mobile cart. The mobile cart may include various elements such as rechargeable power supply in electrical communication with an electric panel providing charging ports for portable electronic devices, converters, transformers and surge protectors for a plurality of AC and DC receptacles as power source for the on-board equipment including one or more computers storing application specific software for the user interface.

The robotic arm 107 may have redundant degrees of freedom allowing for its elbow to be algorithmically, or passively, moved into configurations that are convenient for an operator initiate the positioning of the robotic system or other robotic instrument. For example, the robotic arm may comprise a plurality of joints having redundant degrees of freedom such that the joints of the robotic arm can be driven through a range of differing configurations for a given end effector position (e.g., IDM position). The redundant degrees of freedom may beneficially allow the robotic arm to be self-adjusted to an optimal configuration to avoid collision with other object in the operating environment prior to or during a procedure. For example, the instrument drive mechanism may automatically align itself to a patient side mount (e.g., a support structure at the patient bed for holding and supporting the endoscope device in place) during setup procedure. During the setup procedure and the operation procedure, upon detection of motion of the patient side mount, the instrument drive mechanism (IDM) is able to auto-adjust accordingly to avoid collision while maintain the position of the IDM, eliminating any interruptions to the procedural workflow and avoiding misalignment. In another example, when the robotic arm is actuated during the setup procedure or surgical operation, the system may detect unwanted proximity between any portion of the robotic arm and other objects surrounding it (e.g., the monitor of the system) and the robotic arm may be automatically reconfigured, moved away from the monitor to avoid collision.

In some embodiments, in addition to the autonomous movement of the robotic arm such as automatically positioning the steerable catheter assembly 105 to an initial position (e.g., access point) to access the target tissue, the robot arm may be passively moved by an operator. In such case, an operator can push the arm in any position and the arm compliantly moves. The robotic arm can also be controlled in a compliant mode to improve human robot interaction. For example, the compliant motion control of the robot art may employ a collision avoidance strategy and the position-force control may be designed to save unnecessary energy consumption while reducing impact of possible collisions.

The steerable catheter assembly 105 may comprise a flexible elongate member that is coupled to a handle portion. The robotic endoscope system may comprise an anti-buckling device 101 for preventing the buckling of the elongate member during use.

Figure 2:
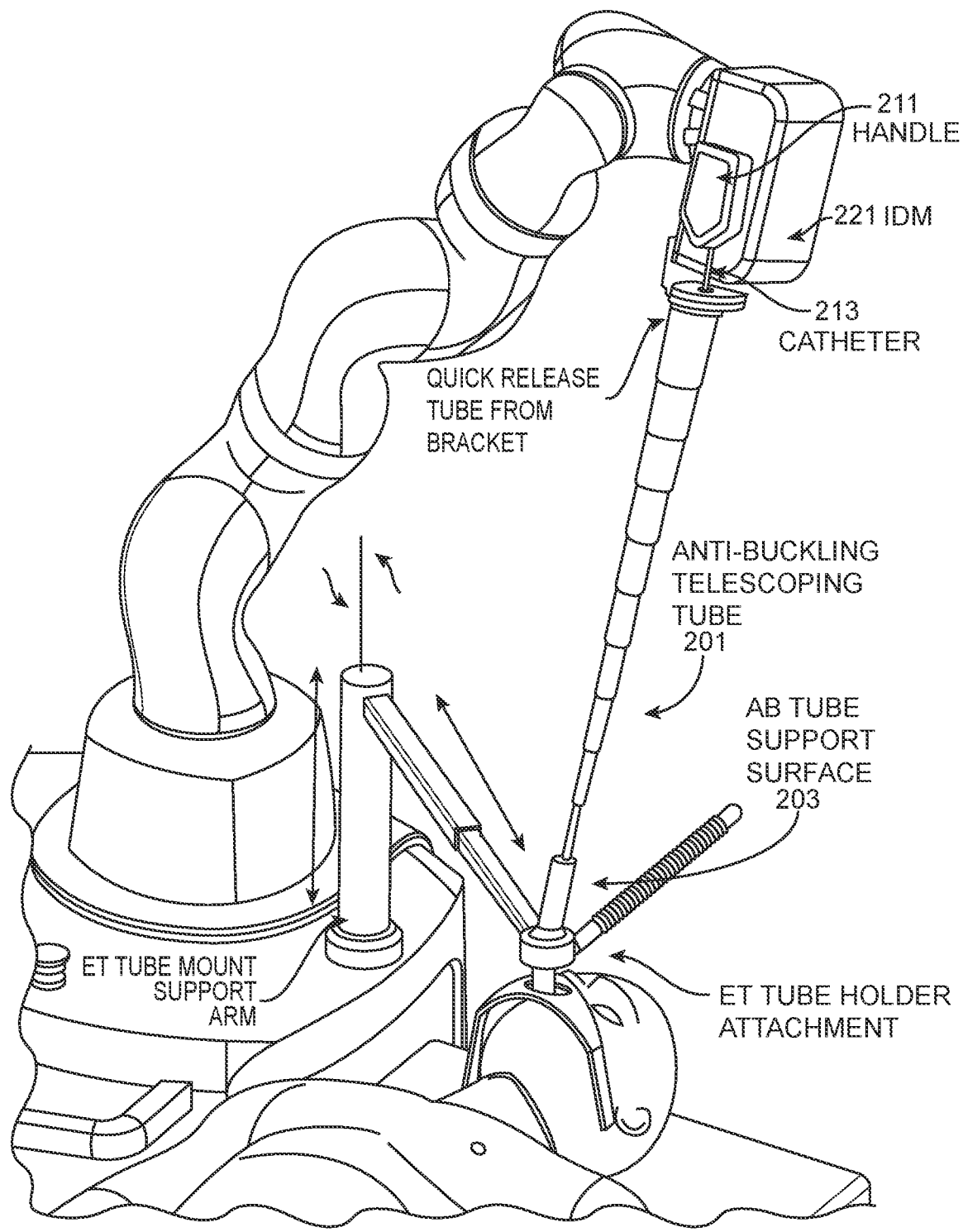
FIG. 2 shows an example of a robotic catheter assembly with an anti-buckling device.

FIG. 2 shows another example of a robotic catheter assembly with an anti-buckling device 201. The steerable catheter assembly may comprise a handle portion 211 that may include components configured to process image data, provide power, or establish communication with other external devices. For instance, the handle portion 211 may include a circuitry and communication elements that enables electrical communication between the steerable catheter assembly and the instrument driving mechanism 221, and any other external system or devices. In another example, the handle portion 211 may comprise circuitry elements such as power sources for powering the electronics (e.g., camera and LED lights) of the endoscope. In some cases, the handle portion may be in electrical communication with the instrument driving mechanism 221 via an electrical interface (e.g., printed circuit board) so that image/video data and/or sensor data can be received by the communication module of the instrument driving mechanism and may be transmitted to other external devices/systems. Alternatively or in addition to, the instrument driving mechanism 221 may provide a mechanical interface only. The handle portion may be in electrical communication with a modular wireless communication device or any other user device (e.g., portable/handheld device or controller) for transmitting sensor data and/or receiving control signals.

The steerable catheter assembly may comprise a flexible elongate member 213 (i.e., catheter) that is coupled to the handle portion 211. In some embodiments, the flexible elongate member may comprise a shaft, steerable tip and a steerable section. The steerable catheter assembly may be a single use robotic endoscope. In some cases, only the elongate member may be disposable. In some cases, at least a portion of the elongate member (e.g., shaft, steerable tip, etc) may be disposable. In some cases, the entire steerable catheter assembly including the handle portion and the elongate member can be disposable. The flexible elongate member and the handle portion are designed such that the entire steerable catheter assembly can be disposed of at low cost.

The robotic endoscope can be releasably coupled to an instrument driving mechanism 221. The instrument driving mechanism 221 may be mounted to the arm of the robotic support system or to any actuated support system as described above. The instrument driving mechanism may provide mechanical and electrical interface to the robotic endoscope. The mechanical interface may allow the robotic endoscope to be releasably coupled to the instrument driving mechanism. For instance, the handle portion of the robotic endoscope can be attached to the instrument driving mechanism via quick install/release means, such as magnets and spring-loaded levels. In some cases, the robotic endoscope may be coupled or released from the instrument driving mechanism manually without using a tool. In some embodiments, the instrument driving mechanism 221 may comprise a set of motors that are actuated to rotationally drive a set of pull wires of the catheter. The handle portion 211 of the catheter assembly may be mounted onto the instrument drive mechanism so that its pulley assemblies are driven by the set of motors. The number of pulleys may vary based on the pull wire configurations. In some cases, one, two, three, four, or more pull wires may be utilized for articulating the catheter.

The handle portion may be designed allowing the robotic endoscope to be disposable at reduced cost. For instance, classic manual and robotic endoscope may have a cable in the proximal end of the endoscope handle. The cable often includes illumination fibers, camera video cable, and other sensors fibers or cables such as EM sensors, or shape sensing fibers. Such complex cable can be expensive adding to the cost of the endoscope. The provided robotic endoscope may have an optimized design such that simplified structures and components can be employed while preserving the mechanical and electrical functionalities. In some cases, the handle portion of the robotic endoscope may employ a cable-free design while providing a mechanical/electrical interface to the catheter.

In some case, the handle portion may be housing or comprise components configured to process image data, provide power, or establish communication with other external devices. In some cases, the communication may be wireless communication. For example, the wireless communications may include Wi-Fi, radio communications, Bluetooth, IR communications, or other types of direct communications. Such wireless communication capability may allow the robotic bronchoscope function in a plug-and-play fashion and can be conveniently disposed after single use. In some cases, the handle portion may comprise circuitry elements such as power sources for powering the electronics (e.g., camera and LED light source) disposed within the robotic bronchoscope or catheter.

The handle portion may be designed in conjunction with the catheter such that cables or fibers can be eliminated. For instance, the catheter portion may employ a design having a single working channel allowing instruments to pass through the robotic bronchoscope, as well as low cost electronics such as a chip-on-tip camera, illumination sources such as light emitting diode (LED) and EM sensors located at optimal locations in accordance with the mechanical structure of the catheter. This may allow for a simplified design of the handle portion. For instance, by using LEDs for illumination, the termination at the handle portion can be based on electrical soldering or wire crimping alone. For example, the handle portion may include a proximal board where the camera cable, LED cable, and EM sensor cable terminate to while the proximal board connects to the interface of the handle portion and establishes the electrical connections to the instrument driving mechanism. As described above, the instrument driving mechanism is attached to the robot arm (robotic support system) and provide a mechanical and electrical interface to the handle portion. This may advantageously improve the assembly and implementation efficiency as well as simplify the manufacturing process and cost. In some cases, the handle portion along with the catheter may be disposed of after a single use.

In some embodiments, the steerable catheter assembly may have a substantially integral design that one or more components may be integral to the catheter thereby simplifying the assembly, manufacturing process while preserving the kinematic, dynamic performance of the steerable catheter. As shown in the example, the steerable catheter assembly may comprise an elongate member 213 or a probing portion that is brought into proximity to the tissue and/or area that is to be examined. The elongate member 213 may, in some cases, also be referred to as catheter. The catheter 213 may comprise internal structures such as a working channel allowing tools to be inserted through. As an example, the working channel may have a dimension such as diameter of around 2 mm to be compatible with standard tools. The working channel may have any other suitable dimensions based on the application.

The catheter 213 may be composed of suitable materials for desired flexibility or bending stiffness. In some cases, the materials of the catheter may be selected such that it may maintain structural support to the internal structures (e.g., working channel) as well as being substantially flexible (e.g., able to bend in various directions and orientations). For example, the catheter can be made of any suitable material such as urethane, vinyl (such as polyvinyl chloride), Nylon (such as vestamid, grillamid), pellethane, polyethylene, polypropylene, polycarbonate, polyester, silicon elastomer, acetate and so forth. In some cases, the materials may be polymer material, bio-compatible polymer material and the catheter may be sufficiently flexible to be advancing through a path with a small curvature without causing pain to a subject. In some cases, the catheter may comprise a sheath. The sheath may not be the same length of the catheter. The sheath may be shorter than the catheter to provide desired support. Alternatively, the catheter may be substantially a single-piece component.

In some case, the distal portion or tip of the catheter may be substantially flexible such that it can be steered into one or more directions (e.g., pitch, yaw). In some embodiments, the catheter may have variable bending stiffness along the longitudinal axis direction. For instance, the catheter may comprise multiple segments having different bending stiffness (e.g., flexible, semi-rigid, and rigid). The bending stiffness may be varied by selecting materials with different stiffness/rigidity, varying structures in different segments, adding additional supporting components or any combination of the above. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires. The distal portion of the catheter may be made of any suitable material such as co-polymers, polymers, metals or alloys such it can be bent by the pull wires. In some embodiments, the proximal end or portion of one or more pull wires may be operatively coupled to various mechanisms (e.g., gears, pulleys, etc.) in the handle portion of the catheter assembly. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end or portion of one or more pull wires may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

As described above, the pull wires may be made of any suitable material such as stainless steel (e.g. SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter or the interstitials of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

In some embodiments, the catheter may be designed to be flexible. When the flexible portions of catheter are inserted by extending mechanisms through endoscope into patients, one or more sections may bend or buckle.

The anti-buckling mechanism 201 may be coupled to the handle portion of the robotic endoscope to support the catheter. The anti-buckling mechanism is used for preventing buckling of the insertion shaft. The anti-buckling mechanism 201 may be a telescopic extending device with internal mechanism to achieve anti-buckling of catheter during the insertion and withdrawal. The anti-buckling mechanism may be detachably connected to the handle portion of the robotic bronchoscope at one end, and may be detachably connected to a support surface 203 at the other end. As shown in the example, the anti-buckling tube may be attached to a bracket on the instrument driving mechanism and may be removable and disposable after the procedure via quick release mechanism. In the examples illustrated in FIG. 2, a support arm (e.g., ET tube mount support arm) may be supported by the robotic mobile cart that supports the endotracheal tube mount and provides a support surface for the distal end of the anti-buckling tube to press against as it is compressed. The support arm may be controlled to rotate, translate vertically up and down and/or may a boom arm that expands and contracts, such that it can be precisely positioned over the patients mouth and attached to the endotracheal tube mount. The support arm positioning may be synchronized with the movement of the robotic arm that it may track the location of the point of entry of the catheter.

The anti-buckling mechanism may require a relatively linear trajectory to be traveled. In some cases, such trajectory may be ensured via an alignment between the anti-buckling mechanism in a collapsed state and a patient-side connector. FIG. 1 shows an example of a patient side connector 121 and IDM 103. For example, the patient-side connector may be fixed to a patient side mount 123 (e.g., attached to the patient bed). The alignment between the IDM and the patient side connector/mount may involve lining up a collapsed anti-buckling mechanism with the patient-side connector. The robotic arm may automatically move the IDM into a position such that the IDM is aligned to the patient-side connector. In some cases, the alignment may comprise generating a 3D depth map of the operating environment, moving the mobile cart into a desired position relative to the patient bed based on the depth map, and moving the IDM into a position and orientation in alignment with the patient-side connector based on a detection of the location/position of the patient-side connector.

Figure 3:
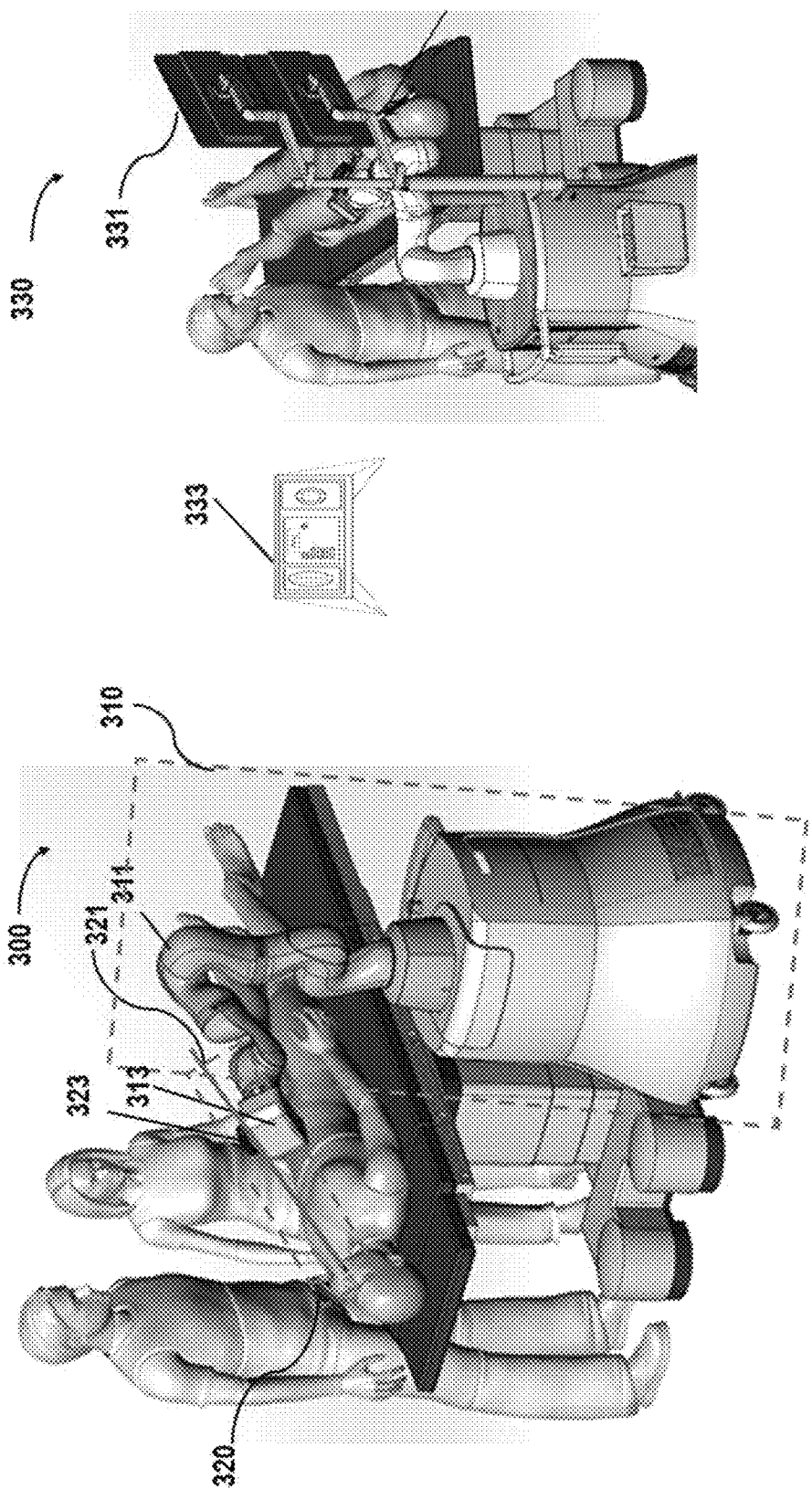
FIG. 3 show examples of robotic endoscope (e.g., bronchoscopy) system capable of performing autonomous collision avoidance and self-alignment before and during operation.

FIG. 3 show examples of robotic endoscope (e.g., bronchoscopy) system capable of performing autonomous collision avoidance and self-alignment before and during operation 300, 330. The robotic endoscope (e.g., bronchoscopy) system 300 may comprise a steerable catheter assembly 320 and a robotic support system 310, for supporting or carrying the steerable catheter assembly. In some cases, the steerable catheter assembly may be a bronchoscope. The steerable catheter assembly can be the same as the endoscope device as described elsewhere herein. In some cases, the steerable catheter assembly may be a single-use robotic bronchoscope. In some embodiments, the robotic endoscope (e.g., bronchoscopy) system 300 may comprise an instrument driving mechanism (IDM) 313 that is attached to the end of the robotic arm 311 of the robotic support system. The instrument driving mechanism may be provided by any suitable controller device (e.g., hand-held controller) that may or may not include a robotic system. The instrument driving mechanism may provide mechanical and electrical interface to the steerable catheter assembly 320. The mechanical interface may allow the steerable catheter assembly 320 to be releasably coupled to the instrument driving mechanism. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

The steerable catheter assembly 320 may comprise a handle portion 323 that may include components configured to processing image data, provide power, or establish communication with other external devices. For instance, the handle portion 323 may include a circuitry and communication elements that enables electrical communication between the steerable catheter assembly 320 and the instrument driving mechanism 313, and any other external system or devices. In another example, the handle portion 323 may comprise circuitry elements such as power sources for powering the electronics (e.g. camera and LED lights) of the endoscope. In some cases, the handle portion may be in electrical communication with the instrument driving mechanism 313 via an electrical interface (e.g., printed circuit board) so that image/video data and/or sensor data can be received by the communication module of the instrument driving mechanism and may be transmitted to other external devices/systems. Alternatively or in addition to, the instrument driving mechanism 313 may provide a mechanical interface only. The handle portion may be in electrical communication with a modular wireless communication device or any other user device (e.g., portable/hand-held device or controller) for transmitting sensor data and/or receiving control signals.

The steerable catheter assembly 320 may comprise a flexible elongate member 321 that is coupled to the handle portion. In some embodiments, the flexible elongate member may comprise a shaft, steerable tip and a steerable section. The steerable catheter assembly may be a single use robotic bronchoscope. In some cases, only the elongate member may be disposable. In some cases, at least a portion of the elongate member (e.g., shaft, steerable tip, etc) may be disposable. In some cases, the entire steerable catheter assembly 320 including the handle portion and the elongate member can be disposable. The flexible elongate member and the handle portion are designed such that the entire steerable catheter assembly can be disposed of at low cost.

In some embodiments, the provided bronchoscope system may also comprise accessories such as a user interface. As illustrated in the example system 330, during operation, one or more components of the system such as a treatment interface module 331 (user console side) and/or a treatment control module 333 (patient and robot side) may be brought into the operating environment. The one or more components or accessories may be added or removed from the operating environment before or during a surgical operation. The robotic arm 311 may have redundant degrees of freedom such that the joints of the robotic arm can be driven into a range of differing configurations for a given end effector position. For example, upon detection of a treatment interface module 311, the robotic arm 311 may automatically move into a different configuration to avoid collision with the treatment interface module while the distal end of the arm of the IDM 313 maintains a particular state (e.g., a given position or velocity of the end effector). Details about the collision avoidance is described later herein.

The treatment interface module may allow an operator or user to interact with the bronchoscope during surgical procedures. In some embodiments, the treatment control module 333 may be a hand-held controller. The treatment control module 333 may allow a user to control a velocity of the tip of the bronchoscope as described elsewhere herein. The treatment control module may, in some cases, comprise a proprietary user input device and one or more add-on elements removably coupled to an existing user device to improve user input experience. For instance, physical trackball or roller can replace or supplement the function of at least one of the virtual graphical element (e.g., navigational arrow displayed on touchpad) displayed on a graphical user interface (GUI) by giving it similar functionality to the graphical element which it replaces. Examples of user devices may include, but are not limited to, mobile devices, smartphones/cellphones, tablets, personal digital assistants (PDAs), laptop or notebook computers, desktop computers, media content players, and the like. Details about the user interface device and user console are described later herein.

The robotic endoscope platform herein may be able to detect one or more objects in the operating environment surrounding the robotic endoscope system. In the cases, the detection of the operating environment may comprise generating an obstacle map. An obstacle map may be a three-dimensional (3D) map describing positions of objects detected in the 3D space.

The 3D map of the operating environment may be constructed based on sensing data. In some cases, the sensing data is received from one or more vision sensors, including depth information for the environment. The vision sensor may comprise a camera, a video camera, a three-dimensional (3D) depth camera, a stereo camera, a depth camera, a Red Green Blue Depth (RGB-D) camera, a time-of-flight (TOF) camera, an infrared camera, a charge coupled device (CCD) image sensor, or a complementary metal oxide semiconductor (CMOS) image sensor. For example, the vision sensor can include only one camera (monocular vision sensor). Alternatively, the vision sensor can include two (binocular vision sensor) or more cameras. The vision sensors may be disposed on the robotic endoscope system such as the robotic cart, the monitor and the like. Alternatively or additionally, the vision sensors may not be disposed on the robotic endoscope system. For instance, the vision sensors may be disposed on the walls, ceilings or other places in the operating environment (e.g., room). In embodiments where multiple vision sensors are used, each sensor can be located on a different portion of the robotic endoscope system, and the disparity between the image data collected by each sensor can be used to provide depth information for the environment. Depth information can be used herein to refer to information regarding distances of one or more objects from the robotic endoscope system and/or sensor. In embodiments where a single vision sensor is used, depth information can be obtained by capturing image data for a plurality of different positions and orientations of the vision sensor, and then using suitable image analysis techniques (e.g., structure from motion) to reconstruct the depth information.

Figure 4A:
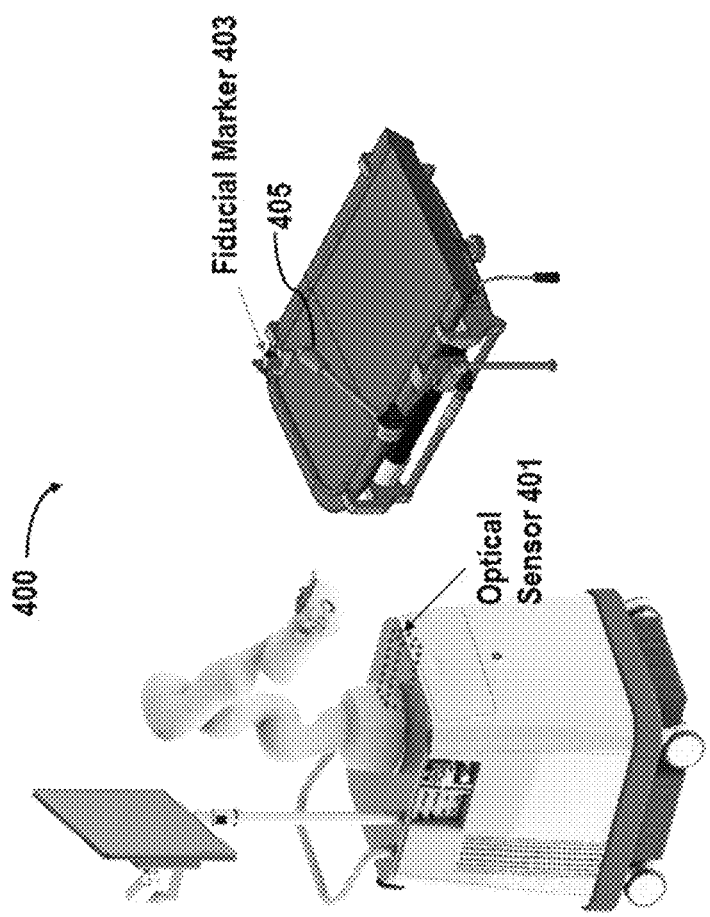
FIG. 4A shows an example of constructing a 3D map of the operating environment using optical sensor.

FIG. 4A shows an example of constructing a 3D map of the operating environment 400 using optical sensor 401 such as a camera. As mentioned elsewhere herein, an operating environment of the system may generally comprise an environment external to the system (e.g., the room the system is in, within certain proximity, etc.) or the environment that the system can move or operate within. In some cases, the camera may be a plenoptic camera having a main lens and additional micro lens array (MLA). The plenoptic camera model may be used to calculate a depth map of the captured image data. In some cases, the image data captured by the camera may be grayscale image with depth information at each pixel coordinate (i.e., depth map). The camera may be calibrated such that intrinsic camera parameters such as focal length, focus distance, distance between the MLA and image sensor, pixel size and the like are obtained for improving the depth measurement accuracy. Other parameters such as distortion coefficients may also be calibrated to rectify the image for metric depth measurement.

In some cases, the image data may be received and processed by one or more processors of the robotic endoscope system. For example, pre-processing of the capture image data may be performed. In an embodiment, the pre-processing algorithm can include image processing algorithms, such as image smoothing, to mitigate the effect of sensor noise, or image histogram equalization to enhance the pixel intensity values. Next, optical approaches as described elsewhere herein may be employed to generate a depth map of the operating environment 400. In some cases, computer vision (CV) techniques or computer vision systems may be used to process the sensing data to extract high-level understanding of the operating environment, object detection, object classification, extraction of the scene depth and estimation of relative positions of objects, extraction of objects' orientation in space. For example, the CV output data may be generated using passive methods that only require images. Passive methods may include, for example, object recognition, stereoscopy, monocular shape-from-motion, shape-from-shading, and Simultaneous Localization and Mapping (SLAM). Alternatively, active methods may be utilized which may require controlled light to be projected into the target scene and the active methods may include, for example structured light and Time-of-Flight (ToF). In some cases, computer vision techniques such as optical flow, computational stereo approaches, iterative method combined with predictive models, machine learning approaches, predictive filtering or any non-rigid registration methods may be used to generate the descriptions of the 3D scene.

In some cases, a fiducial marker 403 may be employed to align the IDM to a patient side mount. The fiducial marker may be placed on the patient bed or the patient side mount 405. The fiducial marker may have a 2D shape or pattern. For example, the fiducial marker may be a 2D QR code, grids, or any asymmetric shape. By acquiring images of the 2D fiducial marker (e.g., from different angles), the location and orientation of the patient side mount that the fiducial marker is placed at in a camera frame can be determined (e.g., triangulation). Based on the known spatial relationship between the camera and the IDM, the orientation and location of the IDM with respect to the patient side mount can be calculated. Alternatively, the fiducial marker may be a 3D fiducial marker such that the marker is visible and discernable in a wide range of angels. For example, a 3D fiducial marker may be located within the view of the imaging system such that the fiducial marker is always discernable regardless the position of the optical sensor with respect to the patient bed or the marker. The fiducial marker(s) may have any suitable 2D/3D shape (non-isotropic) or pattern such that a projection of the fiducial mark(s) corresponding to a view/angle is discernable from that of another view/angle. Alternatively, the alignment of the IDM to the patient side mount may not require the fiducial marker. For instance, the patient side mount may be recognized using segmentation, and/or object recognition method as described elsewhere herein without the fiducial marker. In some cases, a 3D fiducial marker may be utilized to align the IDM to the patient side mount independent of using 3D point cloud. For example, sequence of image frames or video may be acquired containing the fiducial marker and may be processed to identify a spatial relationship (e.g., orientation, position) between the imaging device and patient side mount (i.e., fiducial marker). Based on a known geometric relationship between the IDM and the imaging device, the spatial relationship between the IDM and the patient side mount may be derived. Alternatively, the fiducial marker may be used in conjunction with a 3D depth map. For example, the object identity (e.g., patient side mount) may be identified by the fiducial marker and the depth data may be assigned to the object based on the 3D depth map. In some cases, the 3D depth map may include a 3D point cloud. Alternatively, the 3D depth map may be generated based on the optical image data. the 3D depth map may comprise at least an object (e.g., fiducial marker) with depth information obtained using optical method as described above.

In some cases, the imaging device may be used in conjunction with other types of sensors (e.g., proximity sensor, location sensor, positional sensor, etc.) to improve accuracy of the location information. For instance, the sensing data may further comprise sensor data from one or more proximity sensors. The proximity sensors can be any suitable type such as ultrasonic sensor (e.g., a wide angle sensor, an array sensor) or light detection and ranging (Lidar) sensor. Lidar can be used to obtain three-dimensional information of an environment by measuring distances to objects. The proximity sensors can also be disposed at the robotic endoscope system. The proximity sensors can be located near the vision sensors. Alternatively, the proximity sensors can be situated on a portion of the robotic endoscope system different from the portions used to carry the vision sensors.

In some cases, the 3D depth map may be generated using a single modality sensor data (e.g., image data, Lidar, proximity data, etc.). Alternatively, the 3D depth map may be generated using multi-modality data. For example, the image data and 3D point cloud generated by the Lidar system may be fused using Kalman filter or deep learning model to generate a 3D map. The 3D map may then be used for automatic alignment of the IDM, self-positioning of the robotic car, collision avoidance and various other functions as described elsewhere herein.

In some embodiments, the autonomous alignment of the IDM to a patient side mount may be based on positioning sensors. For example, the sensor signals may be acquired by electromagnetic coils located on the IDM and electromagnetic coils located on the patient side mount along with an electromagnetic tracking system. The position and orientation of the IDM and the patient side mount may be detected, and the difference may be used to generate a command to move robotic arm thereby achieving an autonomous alignment between the IDM and patient side mount.

Figure 4B:
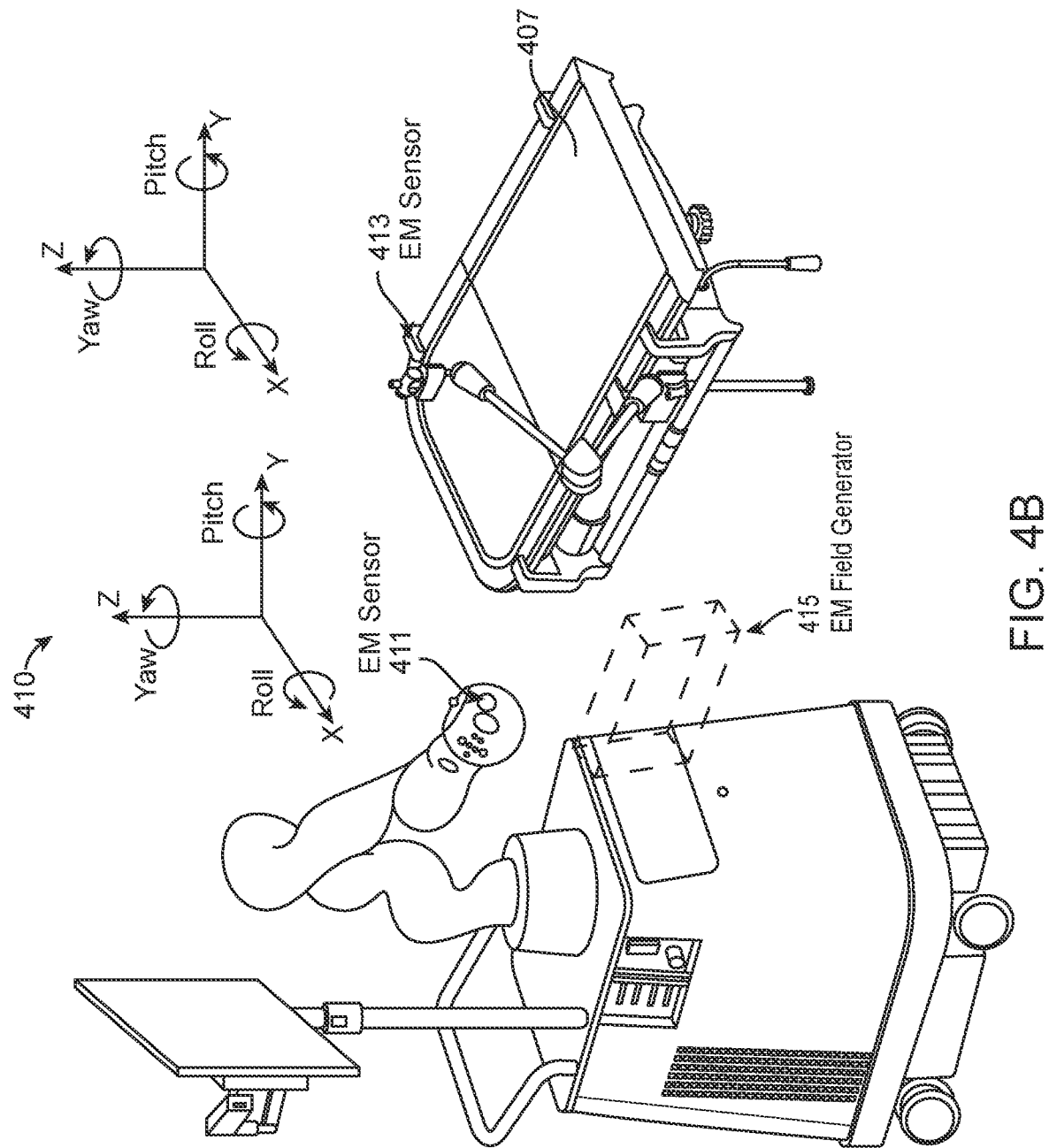

As shown in FIG. 4B, the system may comprise an EM field generator 415 that transmits an EM field in the environment. The EM field generator may be positioned next to the patient torso during procedure, such as on the bed 407, on the robotic cart, or any other suitable place in the environment 410. The system may comprise a first EM sensor 411 located at the IDM to measure position and orientation of the IDM, and a second EM sensor 413 located at the patient side mount to measure position and orientation of the patient side mount. FIG. 4C shows an example of the patient side mount 431 and the associated EM sensors 430. Referring back to FIG. 4B, the EM field generator and the two sets of EM sensors 411, 413 may be utilized by the system to locate the position and orientation of the IDM and the patient side mount in 3D space.

The position and orientation measured by the two sets of EM sensors may be expressed in the filed-generator frame. The EM sensor may be 6 DOF sensor (e.g., X, Y, Z, Roll, Pitch, Yaw) that is able to sense the EM signals generated by the EM field generator and measures the six degrees of freedom spatial data for the IDM and the patient-side-mount. Alternatively, a pair a 5 DOF EM sensors may be located at the IDM and/or the patient side mount to measure the position and orientation. For example, a single 5DOF sensor may generate signals in X, Y, Z, Pitch, and Yaw, without Roll. By placing 2 5DOF sensors inside a device such that they are fixed relative to each other and their center axes are not in parallel with each other, the pair of 5 DOF signals can be used to calculate roll information.

The spatial data about the IDM and the patient side mount may then be processed by the system to determine if the cart is properly positioned for auto-alignment and move the IDM to align with the patient-side-mount such as using a closed-loop-feedback (e.g., controlling robot arm movements to correct the IDM position/orientation based on EM sensor data) and/or other control method as described elsewhere herein.

Figure 5:
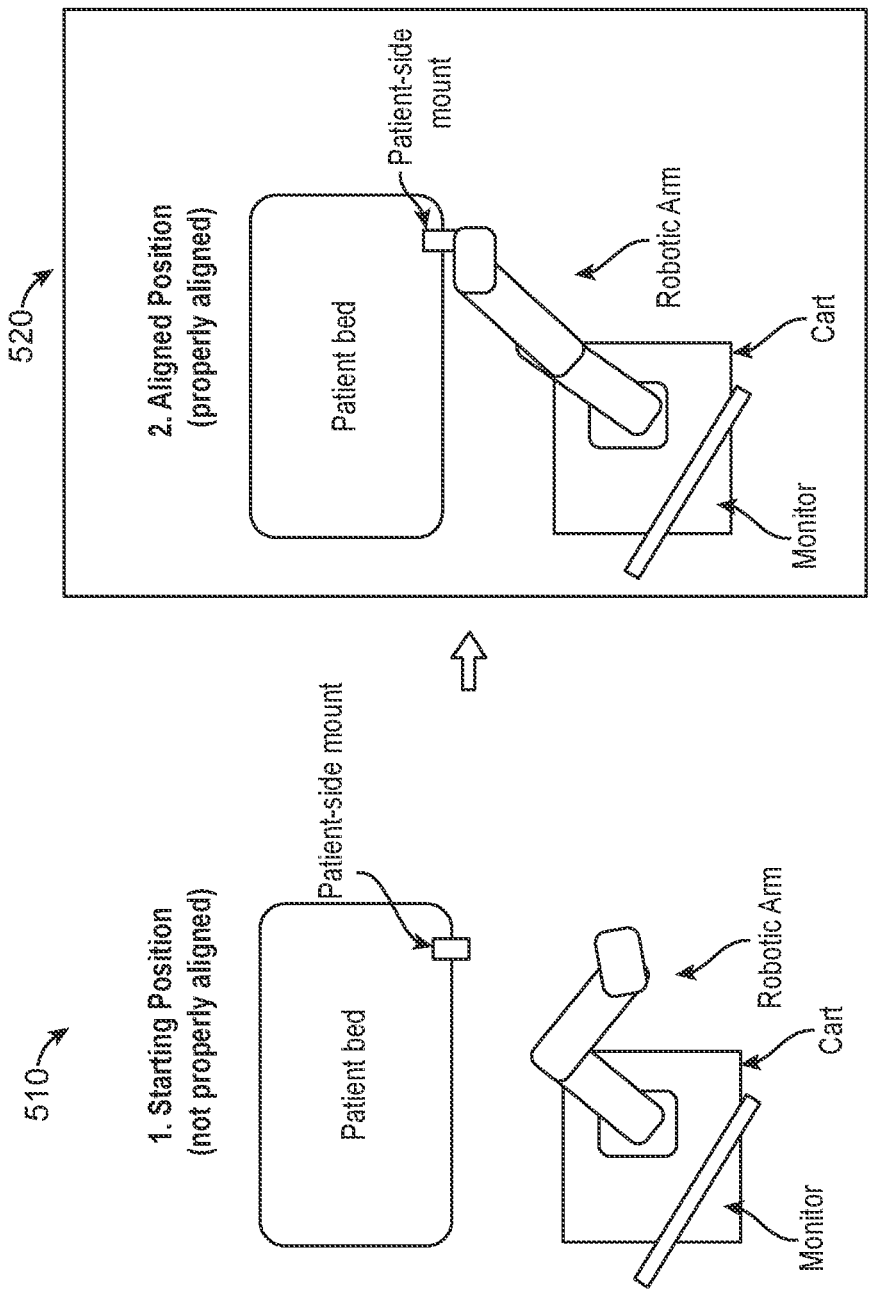
FIG. 5 and FIG. 6 shows an example of autonomous alignment of the IDM (instrument drive mechanism) to a patient side mount.
Figure 6:
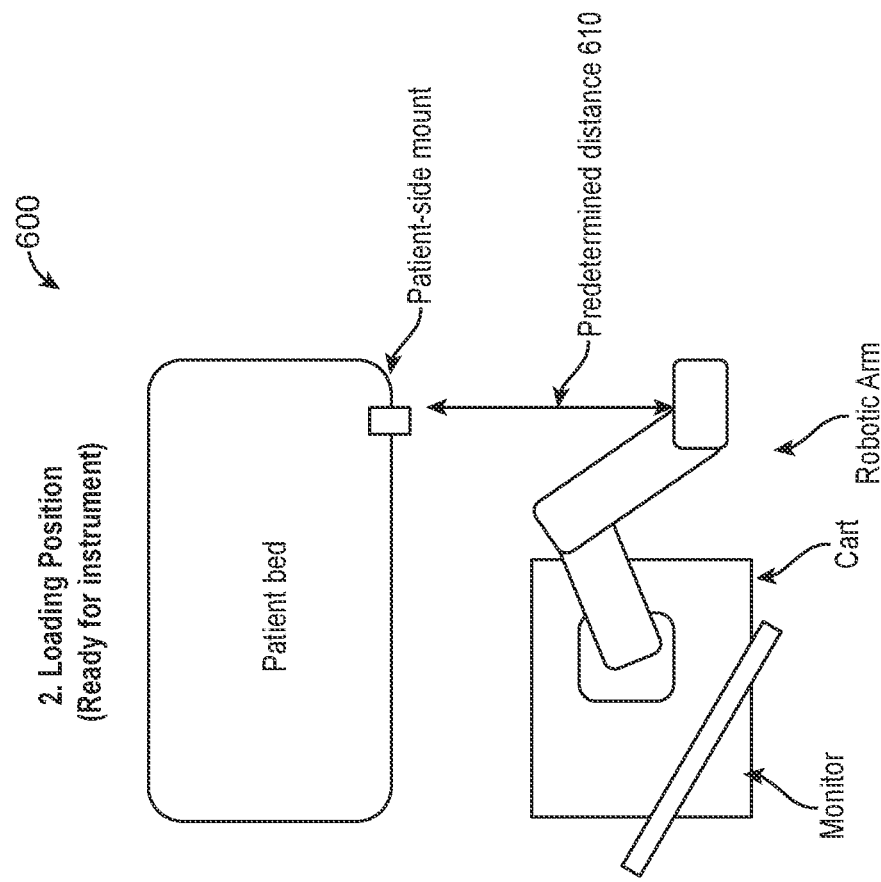

FIG. 5 shows an example of autonomous alignment of the IDM (instrument drive mechanism) to the patient side mount. In the illustrated example 510, the instrument drive mechanism may be initially positioned not in alignment with the patient side mount. During setup procedure, actuators of the plurality of links/joints of the robotic arm may be actuated and automatically align the IDM to the patient side mount 520. In some cases, after alignment, the IDM may be moved to a proper position at a pre-determined distance 610 from the patient side mount 600 for loading an instrument such as the catheter assembly or endoscope device, as shown in FIG. 6. For example, a flexible endoscope apparatus may be coupled to the IDM at the proximal end of the endoscope and coupled to the patient side mount via the connector at the distal end. In some cases, the pre-determined distance 610 may be generated based on a dimension of the endoscope device or empirical data. A user may be permitted to further manually adjust the position of the IDM as needed by switching the robotic arm into a passive mode. For example, once the passive model is enabled, the robotic arm can be placed into any configuration, position or orientation by a user applying force directly and will maintain the desired position and orientation.

As described above, the robotic arm may have redundant degrees of freedom. For instance, the robotic arm may have six, seven, eight, nine or more degrees of freedom (DOF) such that the IDM is able to be oriented in five or six degree of freedom (DOF) space. For example, the robotic arm end effector (e.g., IDM) that can be positioned with six degrees of freedom may in some cases have nine degrees of freedom (six end effector degrees of freedom—three for location, and three for orientation-plus three degrees of freedom to comply with the access site constraints), or ten or more degrees of freedom. Highly configurable robotic arm having more degrees of freedom than are needed for a given end effector position can beneficially sufficient degrees of freedom to allow a range of joint states for an end effector position in a workspace. During the procedure, if there is any motion of the patient side mount, the instrument drive mechanism may be able to auto-adjust accordingly to retain alignment with the patient side mount, eliminating any interruptions to the procedural workflow and avoiding misalignment.

In some embodiments, the 3D depth map generated by the platform may be used for automatic mobile/robotic cart placement. For example, the 3D depth map may comprise description about the operating environment such as identification of equipment, patient bed, human operator, patient and the like and such 3D depth map can be used to generate an optimal location of the mobile cart relative to the patient bed. As described above, computer vision (CV) techniques or computer vision systems may be used to extract high-level understanding of the operating environment, object detection, object classification, extraction of the scene depth and estimation of relative positions of objects, extraction of objects' orientation in space. The 3D map information and sensor data (e.g., proximity sensor, imaging sensor) may be used to detect whether the robotic cart is within an optimal zone with respect to the patient bed.

Figure 7:
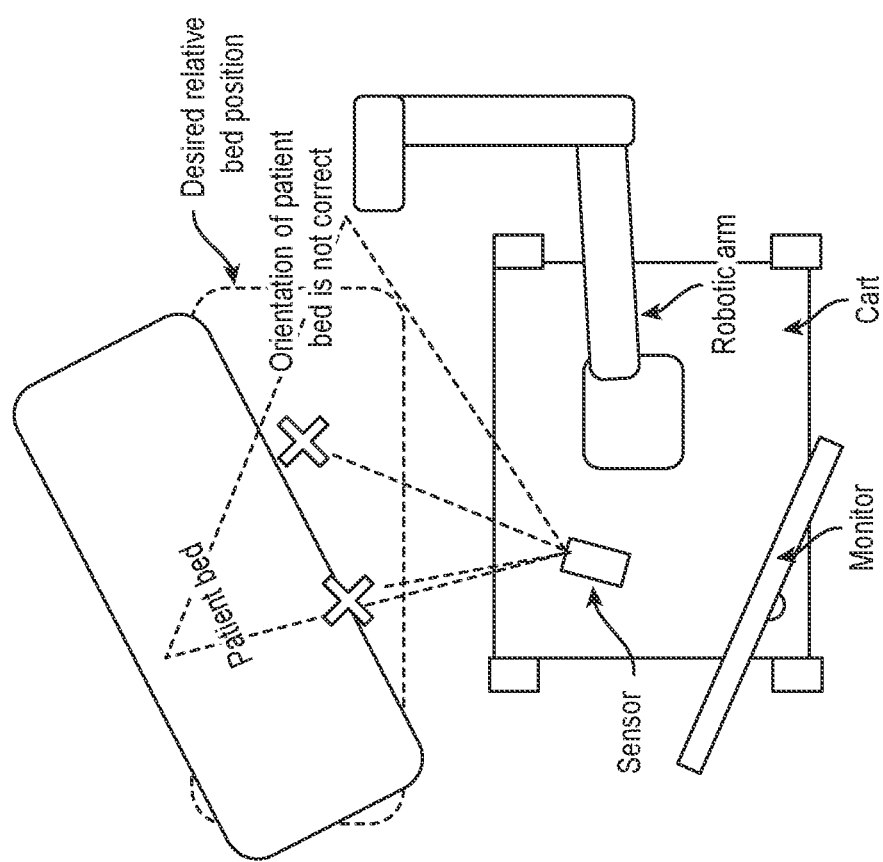
FIG. 7 shows an example of a self-propelled (e.g., via one or more propulsion units such as wheels, rotors, propellers) robotic cart autonomously placing itself with respect to a patient bed.

FIG. 7 shows an example of a self-propelled (e.g., via one or more propulsion units such as wheels, rotors, propellers) robotic cart autonomously placing itself with respect to a patient bed. In some embodiments, a propulsion unit may include a plurality of wheels that may permit the robotic cart to roll over an underlying surface. In some examples, two, three or four wheels may be provided which may permit the robotic cart to stand stably while not moving. In some instances, stabilization may occur with aid of one or more wheels or other stabilization platforms, such as gyroscopic platforms. The wheels may vary in size or be the same size. In some cases, the wheels can have a diameter of at least about 1 cm, 2 cm, 3 cm, 4 cm, 5 cm, 8 cm, 9 cm, 10 cm, 15 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm, 95 cm, 100 cm, 150 cm, or 200 cm. The wheels can have a smooth or treaded surface. The wheels may also permit the robotic cart to move laterally and/or rotate in place. The robotic cart may be capable of making any combination of translational or rotational movement. The propulsion unit may be driven with aid of one or more actuators. For example, a motor, engine, drive train, or any other component may be provided that may aid in driving the propulsion of the robotic cart.

Figure 8:
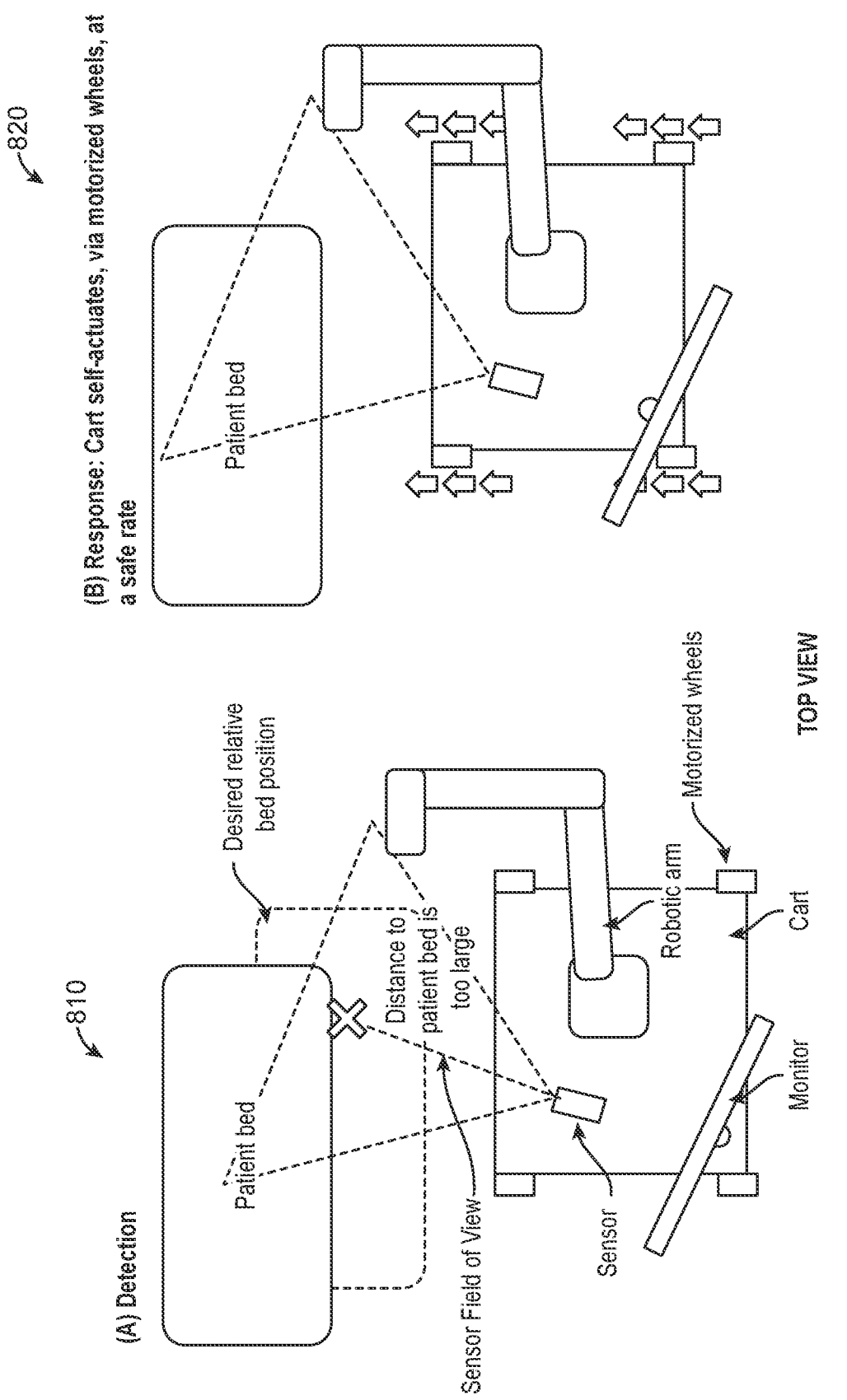
FIG. 8 shows an example of self-alignment of a robotic endoscope system.

Based on the 3D depth map, an optimal location of the robotic cart may be generated. The optimal location may be generated based on a dimension of the robotic cart, the dimension of the robotic arm (workspace), the dimension of the endoscope device and the 3D depth map. Real-time sensor data (e.g., proximity sensor) may be collected and may be used to determine whether the robotic cart is in the proper location relative to the patient bed. As shown in FIG. 8, when the self-propelled robotic cart is detected not in a proper location with respect to the patient bed 810, the robotic cart may automatically move to the proper location 820. The proper location, the movement speed, moving acceleration, and the movement trajectory may be calculated by one or more processors of the platform based at least in part on the 3D depth map.

Alternatively or additionally, the system may inform the user of an non-optimal placement of the robotic cart and may prompt the user to intervene, For instance, message, warning or notification may be displayed on the screen along with recommendations for placing the robotic cart (e.g., specify that the cart should be closer to the bed) and/or displaying a 2D/3D depth map of the operating environment and the robotic system. For example, the robotic system may generate a preferred relative cart position and orientation, respective to the current cart position and display an animation to a user to guide the user changing the position of the robotic cart.

Figure 9:
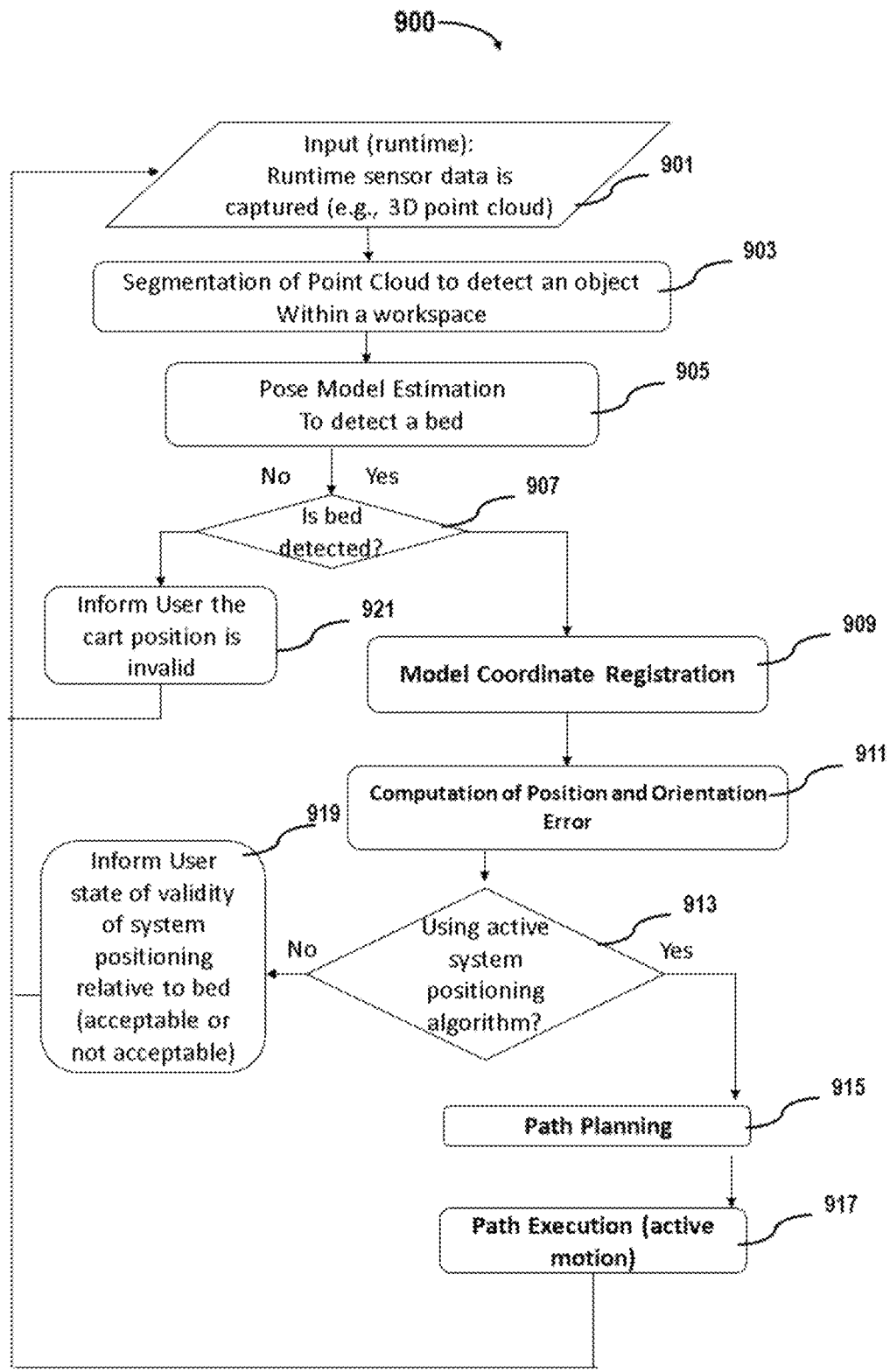
FIG. 9 shows an example process for autonomous alignment of the robotic endoscope system.

FIG. 9 shows an example process 900 for autonomous alignment of the robotic endoscope system. It should be noted that in the illustrated process though Lidar data (e.g., 3D point cloud) is used for the real-time detection of objects in the operating environment and obtaining depth information, any other suitable sensors (e.g., stereoscopic camera) and methods as described elsewhere herein can be utilized. In the exemplary process, runtime sensor data (e.g., 3D point cloud) may be captured as input 901. The runtime sensor data may include data captured by a Lidar (light detection and ranging). The Lidar may obtain three-dimensional information of the operating environment/scene by measuring distances to objects. For example, the emitting apparatus of a Lidar system may generate a sequence of light pulses emitted within short time durations such that the sequence of light pulses may be used to derive a distance measurement point. The Lidar system may provide three-dimensional (3D) imaging (e.g., 3D point cloud). In some cases, the 3D point cloud or the 3D images may be further processed by one or more processors of the robotic endoscope system for obstacles detection or collision avoidance 903. Various suitable image processing method (e.g., image segmentation) may be utilized to recognize an object such as the patient bed. Depth information from the 3D point cloud may be used to assign distances to points within the segmented region (e.g., region of the patient bed).

The positions and orientations of the Lidar sensor may be obtained based on kinematic mapping and such information along with the depth information of the bed is used to estimate relative orientation and position between the bed and the robotic endoscope system. Based on the relative position and orientation, a movement path for moving the robotic cart to an optimal placement with respect to the patient bed may be generated. The optimal placement may be generated by the system automatically without user intervention. In some cases, instead of or in addition to performing the robotic cart self-placement, the algorithm may inform a user an invalid location of the robotic cart relative to the patient bed and a property location of the robotic cart may be displayed to the user on a GUI. The user may be able to provide input via a GUI indicating a selection of the property placement of the robotic cart. Upon receiving the user confirmation, the system may generate the movement path for the robotic cart. Alternatively, a user may be guided to manually move the robotic cart to a desired place as described above.

As described above, any suitable method may be employed to process the real-time sensor data (e.g., 3D point cloud) for segmentation, object recognition and collision avoidance. One or more objects may be segmented in the workspace of the robotic arm. For example, deep learning techniques such as an automated pipeline engine may be provided for processing the lidar data. The pipeline engine may comprise multiple components or layers. The pipeline engine may be configured to preprocess continuous streams of raw Lidar data or batch data transmitted from a Lidar system. In some cases, data may be processed so it can be fed into machine learning analyses. In some cases, data may be processed to provide details at different understanding levels, which understanding may include, by way of non-limiting example, dimensions, weight, composition, identity, degree of collision risk, mobility, and so forth. In some case, the pipeline engine may comprise multiple components to perform different functions for extracting different levels of information from the 3D point cloud data. In some cases, the pipeline engine may further include basic data processing such as, data normalization, labeling data with metadata, tagging, data alignment, data segmentation, and various others. In some cases, the processing methodology is programmable through APIs by the developers constructing the pipeline.

In some embodiments, the pipeline engine may utilize machine learning techniques for processing data. In some embodiments, raw Lidar data may be supplied to a first layer of the pipeline engine which may employ a deep learning architecture to extract primitives, such as edges, corners, surfaces, of one or more target objects. In some cases, the deep learning architecture may be a convolutional neuron network (CNN). CNN systems commonly are composed of layers of different types: convolution, pooling, upscaling, and fully-connected neuron network. In some cases, an activation function such as rectified linear unit may be used in some of the layers. In a CNN system, there can be one or more layers for each type of operation. The input data of the CNN system may be the data to be analyzed such as 3D radar data. The simplest architecture of a convolutional neural networks starts with an input layer (e.g., images) followed by a sequence of convolutional layers and pooling layers, and ends with fully-connected layers. In some cases, the convolutional layers are followed by a layer of ReLU activation function. Other activation functions can also be used, for example the saturating hyperbolic tangent, identity, binary step, logistic, arcTan, softsign, parameteric rectified linear unit, exponential linear unit. softPlus, bent identity, softExponential, Sinusoid, Sinc, Gaussian, the sigmoid function and various others. The convolutional, pooling and ReLU layers may act as learnable features extractors, while the fully connected layers acts as a machine learning classifier.

In some cases, the convolutional layers and fully-connected layers may include parameters or weights. These parameters or weights can be learned in a training phase. The parameters may be trained with gradient descent so that the class scores that the CNN computes are consistent with the labels in the training set for each 3D point cloud image. The parameters may be obtained from a back propagation neural network training process that may or may not be performed using the same hardware as the production or application process.

A convolution layer may comprise one or more filters. These filters will activate when they see same specific structure in the input data. In some cases, the input data may be 3D images, and in the convolution layer one or more filter operations may be applied to the pixels of the image. A convolution layer may comprise a set of learnable filters that slide over the image spatially, computing dot products between the entries of the filter and the input image. The filter operations may be implemented as convolution of a kernel over the entire image. A kernel may comprise one or more parameters. Results of the filter operations may be summed together across channels to provide an output from the convolution layer to the next pooling layer. A convolution layer may perform high-dimension convolutions. For example, the three-dimensional feature maps or input 3D data are processed by a group of three-dimensional kernels in a convolution layer.

The output produced by the first layer of the pipeline engine may be supplied to a second layer which is configured to extract understanding of a target object such as shapes, materials, sub-surface structure and the like. In some cases, the second layer can also be implemented using a machine learning architecture.

The output produced by the second layer may then be supplied to a third layer of the pipeline engine which is configured for perform interpretations and decision makings, such as object recognition, separation, segmentation, collision avoidance, target dynamics (e.g., mobility), identity recognition, type classification and the like. In some cases, the dynamics or mobility of an object may be used for determining a collision avoidance scheme.

The pipeline engine described herein can be implemented by one or more processors. In some embodiments, the one or more processors may be a programmable processor (e.g., a central processing unit (CPU), a graphic processing unit (GPU), a general-purpose processing unit or a microcontroller), in the form of fine-grained spatial architectures such as a field programmable gate array (FPGA), an application-specific integrated circuit (ASIC), and/or one or more Advanced RISC Machine (ARM) processors. In some embodiments, the processor may be a processing unit of a computer system.

In some cases, to mitigate for noise effects, Bayesian estimation techniques (e.g. Kalman filtering) is applied to fit a point cloud to a rigid model of the bed for aligning the robotic cart to the bed. In some cases, if the target object (e.g., patient bed) is not detected 907, the process may proceed with informing user that the robotic cart position is invalid (e.g., out of the proper region) 921. For example, if the bed is not detected, a notification may be displayed on the GUI to inform the user that the cart position is invalid.

If a target object such as a patient bed is detected 907, the method may proceed with model coordinate registration 909 by mapping the position and orientation of the patient bed model to the coordinates of the robotic system (e.g., via a pre-registration of the sensor and robotic system coordinate frames). Next, the method may comprise an algorithm to determine whether the system is in an acceptable workspace. As an example, the algorithm may include computing the position and orientation error 911 and compare it against a threshold to determine whether the system is in an acceptable workspace.

In some cases, the system may provide both an autonomous mode and a manual positioning mode. If autonomous mode once is enabled (e.g., selected by a user) 913, the system may execute an active system positioning algorithm. The active system positioning algorithm may, for example, perform path planning 915 to generate a path from current position to a target position at a target orientation, with proper moving speed, acceleration, and the like. For instance, a robotic cart wheel path plan is generated, or updated, to eliminate the relative orientation error between the desired and the sensed orientation that is computed in the previous operation 911. The path is executed 917 and the robotic wheel motion is controlled to move the robotic cart to the desired orientation and position.

If the system disables the active system positioning algorithm such as in a semi-autonomous mode 913, the user may be informed of the state of validity of the system positioning relative to the bed e.g., acceptable or not acceptable position 919, and the user may manually control the position of the robotic cart.

Figure 10:
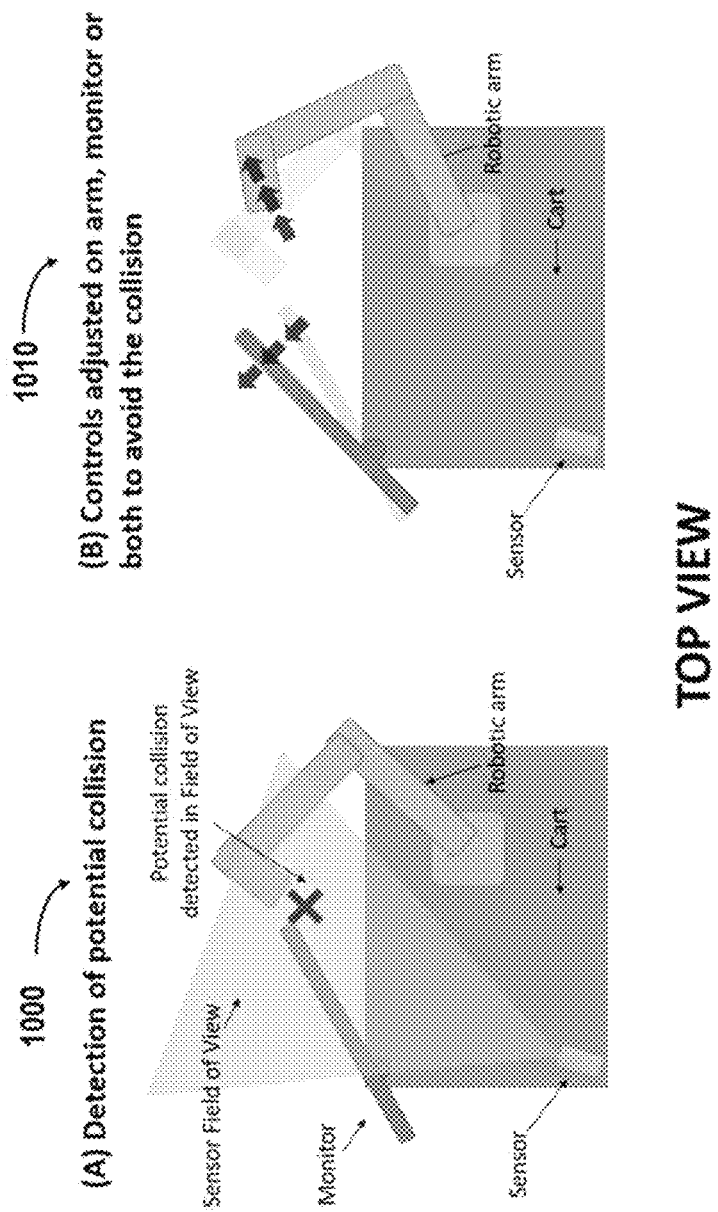
FIGS. 10-12 show examples of collision avoidance of the robotic endoscope system with respect to one or more objects in the operating environment before and during a surgical operation.
Figure 11:
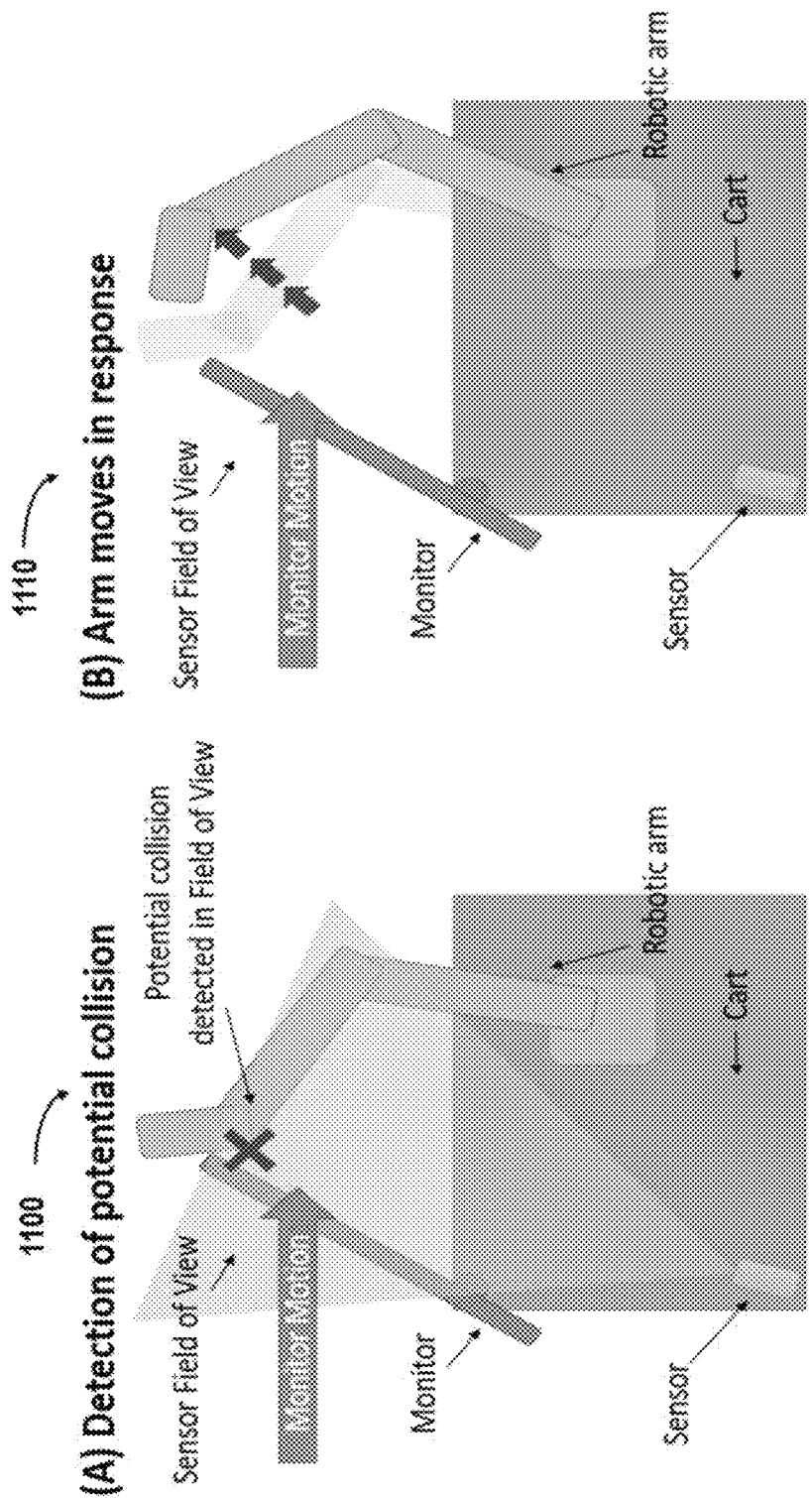
Figure 12:
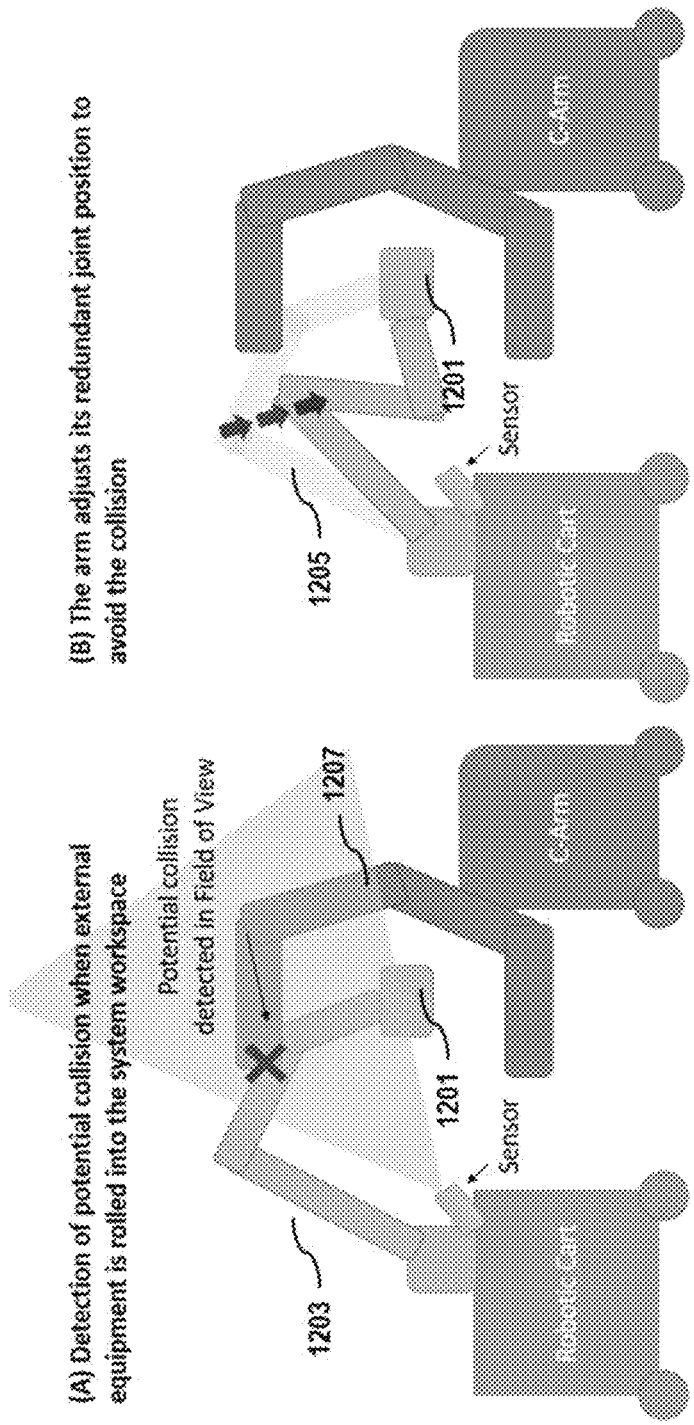

FIGS. 10-12 show examples of collision avoidance. As described above, the real-time 3D map of the operating environment may comprise obstacle information and relative location to one or more components of the robotic endoscope system. The system may determine a proximity threshold and may autonomously move one or more components of the system to avoid collision. For example, as shown in FIG. 10, when the robotic arm is actuated during the procedure, the sensor may detect unwanted proximity between the arm and the monitor of the system 1000. The proximity is detected via the analysis of sensor signals that may contain depth information. In response to the proximity, the user may be informed of the potential collision via a UI warning. Alternatively or additionally, the robotic arm may be automatically moved away from the monitor, or the monitor may be actuated away from the arm 1010. For example, the monitor may be mounted to a robotic support that can be actuated to move the monitor in response to control signals. As illustrated in the example 1010, upon detection of potential collision between the monitor and any portion of the robotic arm, both the robotic support for the monitor and the robotic arm may be actuated to move away from each other. Alternatively, as illustrated in FIG. 11, upon detection of potential collision between the monitor and any portion of the robotic arm 1100, the robotic arm may be actuated to move away from the monitor.

FIG. 11 shows an example when an operator moves a monitor into the workspace of the robotic arm, the system may detect a proximity to the monitor is approaching a threshold and may automatically change a configuration of the robotic arm. The redundancy of the robotic arm may beneficially allow for the change of configuration of the robotic arm while maintaining the position and orientation of the IDM. FIG. 12 shows an example that during the procedure, equipment such as the fluoroscopy C-arm 1207 is brought into the workspace. The system may detect the equipment 1207 and a proximity to the equipment, then automatically adjust a configuration of the robotic arm and/or the robotic cart to provide enough clearance for the C-arm to take fluoroscopy images of the patient and/or complete sweep(s) for tomosynthesis. The configuration of the robotic arm may change from a first configuration 1203 to a second configuration 1205 while the position and orientation of IDM 1201 remain the same.

Figure 13:
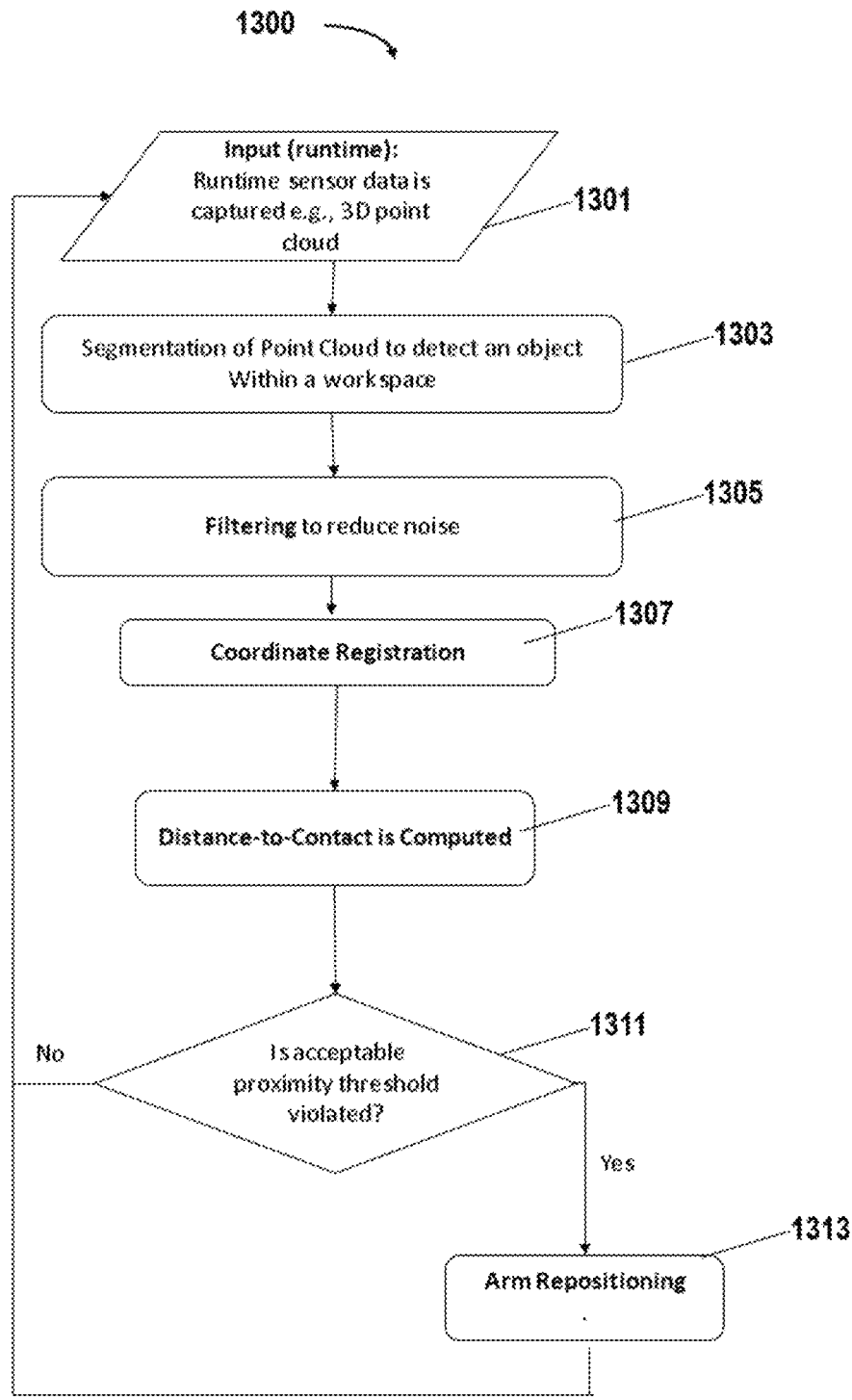
FIG. 13 shows an example of a collision avoidance algorithm.

FIG. 13 shows an example of a collision avoidance algorithm 1300. It should be noted that in the illustrated process though Lidar data (3D point cloud) is used for the real-time detection of objects in the operating environment and obtaining depth information, any other suitable sensors (e.g., stereoscopic camera) and methods as described elsewhere herein can be utilized. The steps about capturing the 3D point cloud data and segmentation of object within a workspace to detect an object can be the same as those described in FIG. 9. For example, the input data may comprise 3D point cloud data captured by Lidar device 1301 and deep learning techniques as described above may be employed to perform object segmentation, object recognition 1303 for collision avoidance. For instance, when an object (e.g., display device, monitor) is brought into the operating environment, a segmentation algorithm may be executed to detect and recognize the object. Depth information from the 3D point cloud may be used to assign distances to points within the segmented region (e.g., region of the monitor).

In some cases, signal filtering is performed to mitigate effects of sensing uncertainty 1305. In some cases, when the object being detected can be represented by a precomputed model, Bayesian filtering methods, such as Kalman filtering, may be applied. For example, the precomputed model may include an estimation algorithm for an object, where the sensed point cloud of a monitor is an input to the estimation algorithm which estimates the state (position, orientation) of a monitoring device.

Next, position and orientation of the point cloud are mapped to arm base coordinate frame 1307. Position of components of the robotic endoscope system such as the robotic arm and position of the points in the segmented monitor region may be registered in the same frame of reference for determining a minimum proximity between any portion of the monitor and any portion of the robotic arm (computing distance-to-contact) 1309. The positions and orientations of the robotic arm may be obtained based on kinematic mapping.

In some cases, a proximity determination algorithm may be executed to determine a potential collision whether the minimum proximity violates a predetermined proximity threshold 1311. In some cases, upon determine a violation of the predetermined proximity threshold, the system may activate an admittance controller to reconfigure a configuration of the robotic arm (e.g., by actuating one or more joints/links of the robotic arm) 1313. For example, the admittance controller may execute an admittance control algorithm which defines a proximal-most point of collision as repulsive force and reconfigure the robotic arm to increase the (minimum) distance between the robotic arm and the monitor. An algorithm is executed to reposition the arm for the purpose of avoiding a collision prior to occurring. In some cases, the admittance control algorithm may map a sensed proximity between any portion of the robotic arm and an object to a virtual force applied on the robotic arm and calculate an output motion for the robotic arm as if an equivalent contact force was applied to the robotic arm (through contact). For instance, the admittance control algorithm comprises mapping a shortest distance between a link of an arm and obstacle to an input to a commanded task-space velocity of the arm link. The Geometric Jacobian of the arm may be used to map a task-space motion command to arm joint commands in order to achieve arm motion which increases the distance between the arm and obstacle.

In the event of the robotic system having more degrees-of-freedom than the task, i.e. actuation redundancy existing, the avoidance may be implemented via a redundancy resolution algorithm. For exempt the elbow of the arm may be repositioned to prevent a collision without affecting the position and orientation of the end-effector. Such algorithm may be implemented by defining a secondary redundancy-resolution task where the arm is repositioned such that the distance between the arm and the object (prior to collision) is increased. In some cases, when there is more than one degree-of-freedom in redundancy, the robot command can be chosen to actuate the joint, for example, as one where the norm of joint rates is minimized.

In some embodiments, the robotic endoscope system may be capable of autonomously adjusting position of the IDM relative to the patient side mount based on buckling detection. When the flexible endoscope is pushed at the proximal end, during insertion of the flexible device into the anatomy, the flexible endoscope may deform when navigating through turns and buckling. The deformation may happen during insertion, as the flexible device may take on a minimum-energy shape, which may be a "hugging" of the shaft against tissue. The buckling may happen when resistance force is encountered in the distal portion of the shaft.

During retraction of the flexible device, the distance of the shaft that is "lost to buckling" may become slack when the system actuation direction is reversed (e.g., backward moving or retraction). This phenomenon will result in a perceived dead-zone or system delay (a user input to command movement of the robotic endoscope tip does not map directly to robotic endoscope tip motion). When an endoscope is buckled, a retraction of the endoscope may result in robotic actuation with little endoscope tip translation.

The prolapse or kink may result in potential damage as it may expose the sharp edges of the kinked elongate device and complicate the surgical procedure. Moreover, a bent or kinked elongate device may render the system losing location/shape control of the device during both insertion and retraction and it may block the passage of an instrument. Furthermore, a device that prolapses or kinks may not be able to provide adequate reach towards the target anatomy for performing the intended task.

The robotic endoscope system herein may employ a responsive insertion and retraction velocity control of the flexible endoscope. The responsive velocity control method herein may automatically correct for motion differences between the endoscope tip and a velocity command (e.g., instrument driving mechanism (IDM) command). In some cases, the velocity control of the endoscope may be performed in conjunction with the collision avoidance algorithm as described above such that the robotic arm may autonomously reconfigure to avoid collision with other objects while the velocity of the endoscope tip is maintained and not influenced.

Unlike the conventional methods for buckling detection based on the difference in the position of the endoscope device (e.g., expected position and measure tip position), the methods and systems herein may automatically correct the buckling/deformation during insertion and retraction based on the velocity measured at an endoscope tip and a velocity control command. This beneficially avoids shape sensing or using extra imaging approaches to determine the shape or position of the endoscope device.

During insertion of an endoscope device, a velocity command may be received by the endoscope device. The velocity command may be provided by a user input. For example, a user may provide a control instruction via a control interface of the endoscope device indicating a desired/expected velocity of the endoscope tip. The control interface may include various devices such as touchscreen monitors, joysticks, keyboards and other interactive devices. A user may be able to navigate and/or control the motion of the robotic arm and the motion (e.g., tip velocity) of the catheter using a user input device. The user input device can have any type user interactive component, such as a button, mouse, joystick, trackball, touchpad, pen, image capturing device, motion capture device, microphone, touchscreen, hand-held wrist gimbals, exoskeletal gloves, or other user interaction system such as virtual reality systems, augmented reality systems and the like.

The user input for commanding a velocity of the endoscope tip may be received via the input device. For instance, a press on a joystick may be mapped to an analog value indicating a speed/velocity of the tip. For example, half press on the joystick may be mapped to 3 mm/s, full press may be mapped to 6 mm/s and no press may be mapped to 0 mm/s.

Based on the specific user input device, the user input may be processed to be converted to a desired/commanded velocity of the tip of the catheter/endoscope. Next, a tip velocity error is computed. The tip velocity error is the difference between the desired/commanded tip velocity and the velocity of the endoscope tip. In some embodiments, the velocity of the endoscope tip may be measured based on sensor data. In some cases, the sensor data may comprise position and orientation information of the distal tip of the endoscope.

In some cases, the sensor signals may be acquired by positioning sensors. For example, the sensor signals may be acquired by electromagnetic coils located on the distal end used with an electromagnetic tracking system to detect the position and orientation of the distal end of the endoscope. For example, positioning sensors such as electromagnetic (EM) sensors may be embedded at the distal tip of the catheter and an EM field generator may be positioned next to the patient torso during procedure. The EM field generator may locate the EM sensor position in 3D space or may locate the EM sensor position and orientation in 5D or 6D space. The endoscope tip position measured by the EM sensor $p_e$=EM sensor (tip) position, may be expressed in field-generator frame.

Next, the linear velocity of the endoscope tip may be computed. The linear velocity may be computed using time derivative method such as backward Euler derivative. In some cases, the endoscope tip velocity may be computed as the filtered time derivative of tip position (e.g., measured by the EM sensor expressed in the filed-generator frame), projected in the heading direction. This projection may be required because the user provided velocity command is based on integrated position changes that occur in the direction of n. In some cases, a low pass filter may be applied to generate the filtered time derivative data.

The endoscope tip velocity may be computed as the filtered time derivative of tip position (e.g., measured by the EM sensor expressed in the filed-generator frame), projected in the heading direction of n using a projection matrix $v_n = nn^T \text{filt}(dp_e/dt)$.

Where n is a unit vector that indicates the endoscope tip heading direction, expressed in field-generator frame. There may be mechanical offset between the EM sensor and the scope tip and the mechanical offset may be calibrated for each endoscope device. $dp_e/dt$ represents the time derivative of the endoscope tip, $nn^T$ is the projection matrix that maps the aforementioned velocity to the heading direction of the endoscope tip (i.e. velocities that are not in the direction of the heading are ignored). The velocity $v_n$ may not be affected by articulation as the endoscope tip translation owing to articulation is orthogonal to n.

After the endoscope tip velocity is computed, the endoscope tip velocity error may be computed and may be further processed for safety checks. In some cases, the safety checks may comprise a plurality of checks. For example, the plurality of checks may comprise determining whether the endoscope tip has been stationary (e.g., tip velocity is about zero) while the handle portion of the endoscope (e.g., IDM) has an insertion distance is beyond a distance threshold. In another example, the plurality of checks may comprise determining whether the endoscope tip is retracting (e.g., negative tip velocity error) while the handle portion of the endoscope (e.g., IDM) is inserting, if yes, a prolapse may be occurring. In a further example, the plurality of checks may comprise determining whether the insertion force is beyond a force threshold. The term "insertion distance" as utilized herein may refer to the distance along the navigation path.

The method may comprise a closed loop control of the tip velocity to reduce the tip velocity error. The tip velocity of the endoscope may be controlled based on the tip velocity error computed at operation which is used as the feedback signal for commanding the motion of the IDM. The user velocity input may be mapped to the command to control the motion of IDM (e.g., velocity to move the IDM along the insertion axis). The command may be control signals to control the motors of the robotic arm thereby controlling a motion of the IDM (i.e., proximal end of the endoscope). The endoscope tip velocity may be calculated based on the robotic arm inverse kinematics. The endoscope tip velocity is then used to calculate the tip velocity in the heading direction by projection in the heading direction of n using a projection matrix as described above. In some cases, the feedback signal may be the projection of tip velocity processed by a low-pass filter.

Based on the control algorithm, a motion command is generated to actuate the robotic arm thereby affecting a tip velocity of the endoscope. The effect on the motion of the IDM (e.g., insertion velocity, insertion distance) and on the motion of the endoscope tip (e.g., tip velocity) may not perfectly match due to the tortuosity of the navigation path, the buckling and/or prolapse as described above.

During retraction of the medical device, a previously determined deformation-loss during insertion may be used as a feed-forward term to perform a backslash compensation for the retraction control. This reduces the deformation-loss incurred during the insertion prior to the tip motion during the retraction.

Figure 14:
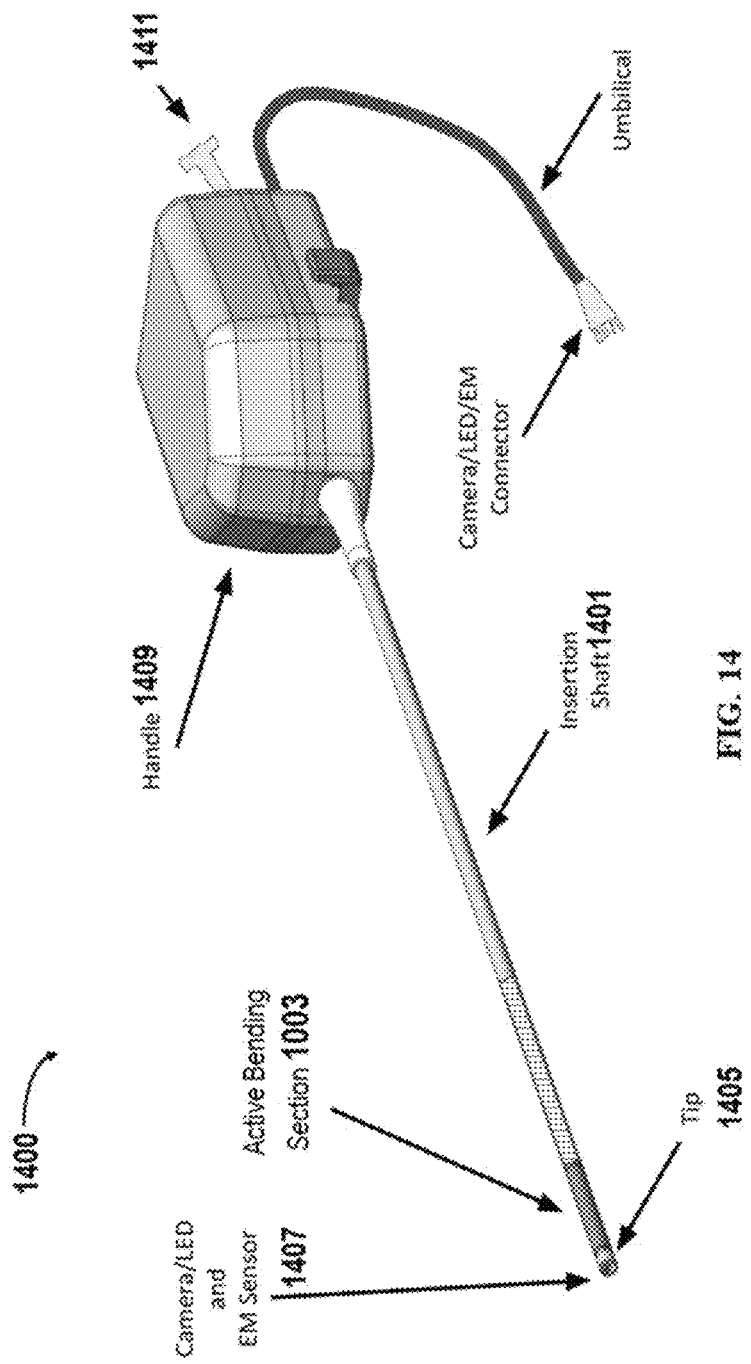
FIG. 14 and FIG. 15 show examples of a flexible endoscope.

FIG. 14 illustrates an example of a flexible endoscope 1400, in accordance with some embodiments of the present disclosure. As shown in FIG. 14, the flexible endoscope 1400 may comprise a handle/proximal portion 1409 and a flexible elongate member to be inserted inside of a subject. The flexible elongate member can be the same as the one described above. In some embodiments, the flexible elongate member may comprise a proximal shaft (e.g., insertion shaft 1401), steerable tip (e.g., tip 1405), and a steerable section (active bending section 1403). The active bending section, and the proximal shaft section can be the same as those described elsewhere herein. The endoscope 1400 may also be referred to as steerable catheter assembly as described elsewhere herein. In some cases, the endoscope 1400 may be a single-use robotic endoscope. In some cases, the entire catheter assembly may be disposable. In some cases, at least a portion of the catheter assembly may be disposable. In some cases, the entire endoscope may be released from an instrument driving mechanism and can be disposed of. In some embodiment, the endoscope may contain varying levels of stiffness along the shaft, as to improve functional operation.

The endoscope or steerable catheter assembly 1400 may comprise a handle portion 1409 that may include one or more components configured to process image data, provide power, or establish communication with other external devices. For instance, the handle portion may include a circuitry and communication elements that enables electrical communication between the steerable catheter assembly 1400 and an instrument driving mechanism (not shown), and any other external system or devices. In another example, the handle portion 1409 may comprise circuitry elements such as power sources for powering the electronics (e.g., camera, electromagnetic sensor and LED lights) of the endoscope.

The one or more components located at the handle may be optimized such that expensive and complicated components may be allocated to the robotic support system, a hand-held controller or an instrument driving mechanism thereby reducing the cost and simplifying the design the disposable endoscope. The handle portion or proximal portion may provide an electrical and mechanical interface to allow for electrical communication and mechanical communication with the instrument driving mechanism. The instrument driving mechanism may comprise a set of motors that are actuated to rotationally drive a set of pull wires of the catheter. The handle portion of the catheter assembly may be mounted onto the instrument drive mechanism so that its pulley/capstans assemblies are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

The electrical interface (e.g., printed circuit board) may allow image/video data and/or sensor data to be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

In some cases, the handle portion 1409 may comprise one or more mechanical control modules such as lure 1411 for interfacing the irrigation system/aspiration system. In some cases, the handle portion may include lever/knob for articulation control. Alternatively, the articulation control may be located at a separate controller attached to the handle portion via the instrument driving mechanism.

The endoscope may be attached to a robotic support system or a hand-held controller via the instrument driving mechanism. The instrument driving mechanism may be provided by any suitable controller device (e.g., hand-held controller) that may or may not include a robotic system. The instrument driving mechanism may provide mechanical and electrical interface to the steerable catheter assembly 1400. The mechanical interface may allow the steerable catheter assembly 1400 to be releasably coupled to the instrument driving mechanism. For instance, the handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

In the illustrated example, the distal tip of the catheter or endoscope shaft is configured to be articulated/bent in two or more degrees of freedom to provide a desired camera view or control the direction of the endoscope. As illustrated in the example, imaging device (e.g., camera), position sensors (e.g., electromagnetic sensor) 1407 is located at the tip of the catheter or endoscope shaft 1405. For example, line of sight of the camera may be controlled by controlling the articulation of the active bending section 1403. In some instances, the angle of the camera may be adjustable such that the line of sight can be adjusted without or in addition to articulating the distal tip of the catheter or endoscope shaft. For example, the camera may be oriented at an angle (e.g., tilt) with respect to the axial direction of the tip of the endoscope with aid of an optimal component.

The distal tip 1405 may be a rigid component that allow for positioning sensors such as electromagnetic (EM) sensors, imaging devices (e.g., camera) and other electronic components (e.g., LED light source) being embedded at the distal tip.

In real-time EM tracking, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. For example, the EM field generator may be positioned close to the patient torso during procedure to locate the EM sensor position in 3D space or may locate the EM sensor position and orientation in 5D or 6D space. This may provide a visual guide to an operator when driving the bronchoscope towards the target site.

The endoscope may have a unique design in the elongate member. In some cases, the active bending section 1403, and the proximal shaft of the endoscope may consist of a single tube that incorporates a series of cuts (e.g., reliefs, slits, etc.) along its length to allow for improved flexibility, a desirable stiffness as well as the anti-prolapse feature (e.g., features to define a minimum bend radius).

As described above, the active bending section 1403 may be designed to allow for bending in two or more degrees of freedom (e.g., articulation). A greater bending degree such as 180 and 270 degrees (or other articulation parameters for clinical indications) can be achieved by the unique structure of the active bending section. In some cases, a variable minimum bend radius along the axial axis of the elongate member may be provided such that an active bending section may comprise two or more different minimum bend radii.

The articulation of the endoscope may be controlled by applying force to the distal end of the endoscope via one or multiple pull wires. The one or more pull wires may be attached to the distal end of the endoscope. In the case of multiple pull wires, pulling one wire at a time may change the orientation of the distal tip to pitch up, down, left, right or any direction needed. In some cases, the pull wires may be anchored at the distal tip of the endoscope, running through the bending section, and entering the handle where they are coupled to a driving component (e.g., pulley). This handle pulley may interact with an output shaft from the robotic system.

In some embodiments, the proximal end or portion of one or more pull wires may be operatively coupled to various mechanisms (e.g., gears, pulleys, capstans, etc.) in the handle portion of the catheter assembly. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end/portion of one or more pull wires may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The pull wires may be made of any suitable material such as stainless steel (e.g., SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The proximal design may improve the reliability of the device without introducing extra cost allowing for a low-cost single-use endoscope. In another aspect of the invention, a single-use robotic endoscope is provided. The robotic endoscope may be a bronchoscope and can be the same as the steerable catheter assembly as described elsewhere herein. Traditional endoscopes can be complex in design and are usually designed to be re-used after procedures, which require thorough cleaning, dis-infection, or sterilization after each procedure. The existing endoscopes are often designed with complex structures to ensure the endoscopes can endure the cleaning, dis-infection, and sterilization processes. The provided robotic bronchoscope can be a single-use endoscope that may beneficially reduce cross-contamination between patients and infections. In some cases, the robotic bronchoscope may be delivered to the medical practitioner in a pre-sterilized package and are intended to be disposed of after a single-use.

Figure 15:
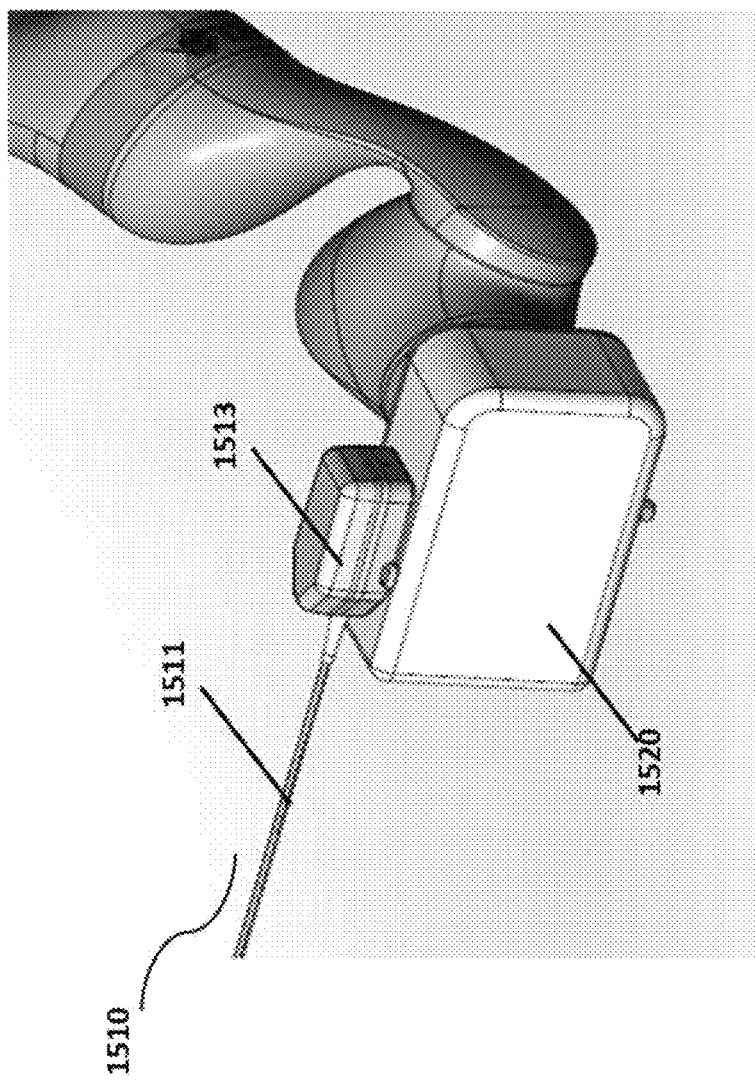

As shown in FIG. 15, a robotic bronchoscope 1510 may comprise a handle portion 1513 and a flexible elongate member 1511. In some embodiments, the flexible elongate member 1111 may comprise a shaft, steerable tip, and a steerable/active bending section. The robotic bronchoscope 1510 can be the same as the steerable catheter assembly as described in FIG. 14. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of. In some cases, the bronchoscope may contain varying levels of stiffness along its shaft, as to improve functional operation. In some cases, a minimum bend radius along the shaft may vary.

The robotic bronchoscope can be releasably coupled to an instrument driving mechanism 1520. The instrument driving mechanism 1520 may be mounted to the arm of the robotic support system or to any actuated support system as described elsewhere herein. The instrument driving mechanism may provide mechanical and electrical interface to the robotic bronchoscope 1510. The mechanical interface may allow the robotic bronchoscope 1510 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

Figure 16:
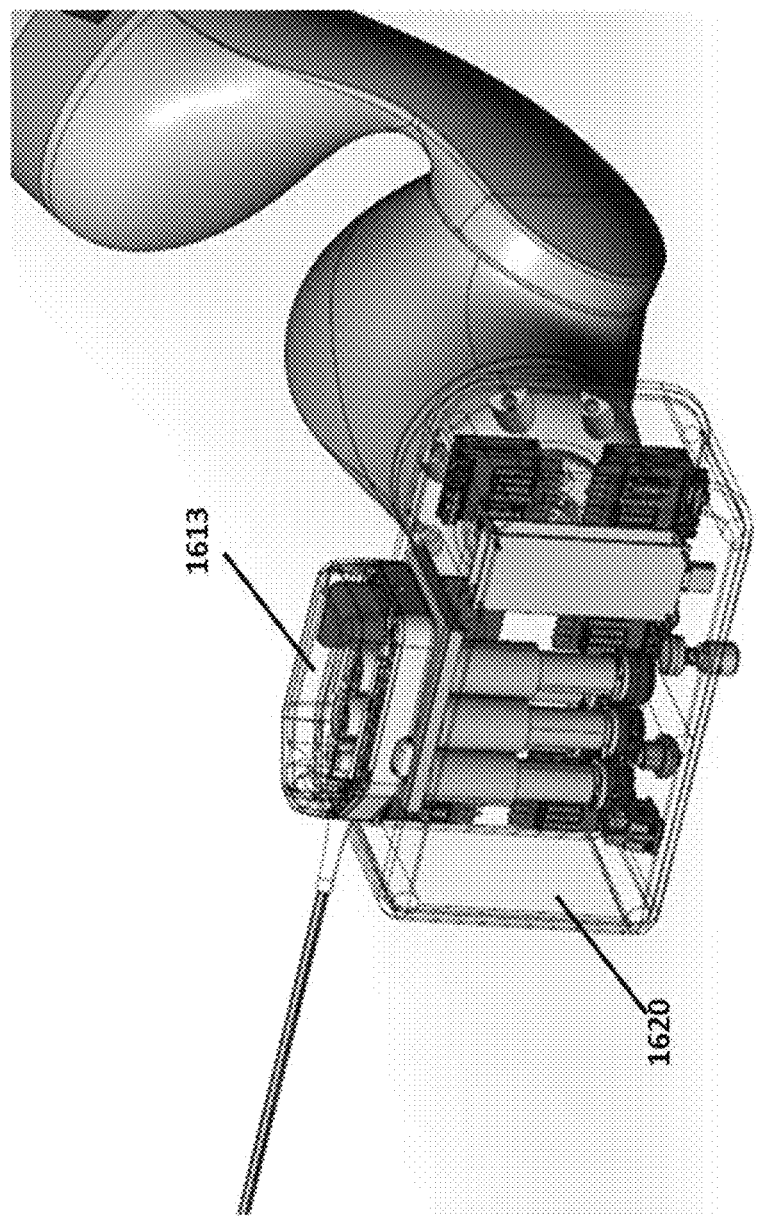
FIG. 16 shows an example of an instrument driving mechanism providing mechanical interface to the handle portion of a robotic bronchoscope.

FIG. 16 shows an example of an instrument driving mechanism 1620 providing mechanical interface to the handle portion 1613 of the robotic bronchoscope. As shown in the example, the instrument driving mechanism 1620 may comprise a set of motors that are actuated to rotationally drive a set of pull wires of the flexible endoscope or catheter. The handle portion 1613 of the catheter assembly may be mounted onto the instrument drive mechanism so that its pulley assemblies or capstans are driven by the set of motors. The number of pulleys may vary based on the pull wire configurations. In some cases, one, two, three, four, or more pull wires may be utilized for articulating the flexible endoscope or catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive, adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

Figure 17:
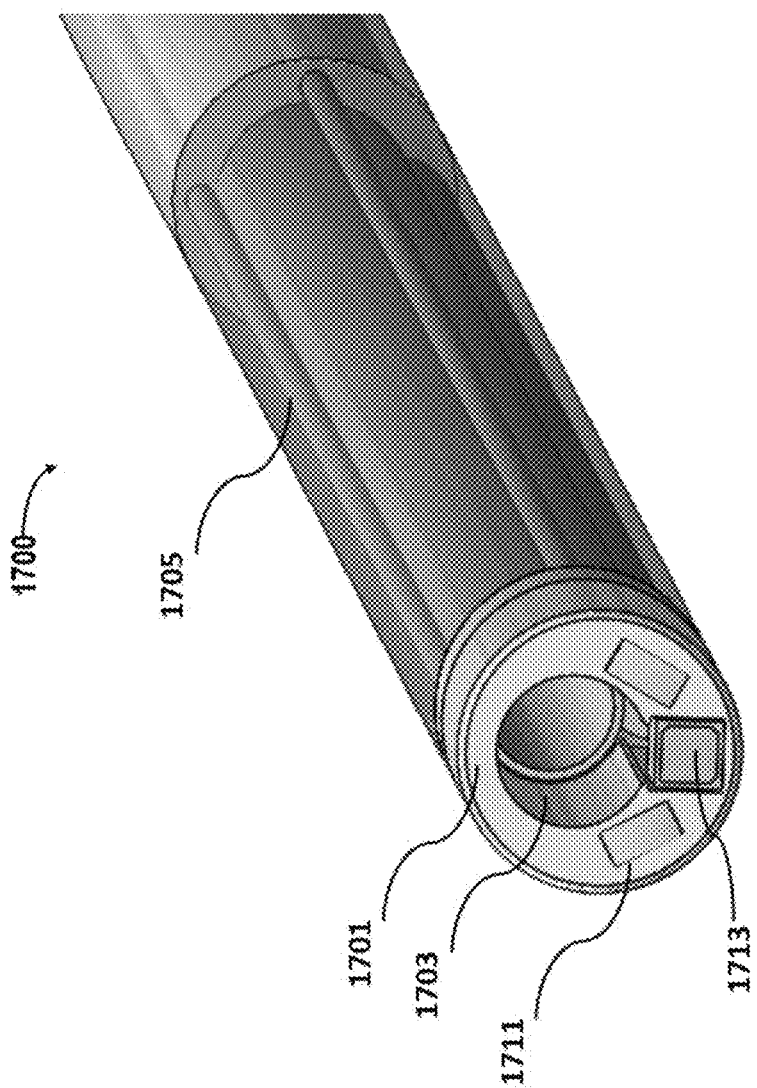
FIG. 17 shows an example of a distal tip of an endoscope.

FIG. 17 shows an example of a distal tip 1700 of an endoscope. In some cases, the distal portion or tip of the catheter 1700 may be substantially flexible such that it can be steered into one or more directions (e.g., pitch, yaw). The catheter may comprise a tip portion, bending section, and insertion shaft. In some embodiments, the catheter may have variable bending stiffness along the longitudinal axis direction. For instance, the catheter may comprise multiple sections having different bending stiffness (e.g., flexible, semi-rigid, and rigid). The bending stiffness may be varied by selecting materials with different stiffness/rigidity, varying structures in different segments (e.g., cuts, patterns), adding additional supporting components or any combination of the above. In some embodiments, the catheter may have variable minimum bend radius along the longitudinal axis direction. The selection of different minimum bend radius at different location long the catheter may beneficially provide anti-prolapse capability while still allow the catheter to reach hard-to-reach regions. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires 1705. The distal portion of the catheter may be made of any suitable material such as co-polymers, polymers, metals or alloys such that it can be bent by the pull wires. In some embodiments, the proximal end or terminal end of one or more pull wires 1705 may be coupled to a driving mechanism (e.g., gears, pulleys, capstan etc.) via the anchoring mechanism as described above.

The pull wire 1705 may be a metallic wire, cable or thread, or it may be a polymeric wire, cable or thread. The pull wire 1705 can also be made of natural or organic materials or fibers. The pull wire 1705 can be any type of suitable wire, cable or thread capable of supporting various kinds of loads without deformation, significant deformation, or breakage. The distal end or portion of one or more pull wires 1705 may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera 1713. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 1711 positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

The imaging device and the illumination device may be integrated to the catheter. For example, the distal portion of the catheter may comprise suitable structures matching at least a dimension of the imaging device and the illumination device. The imaging device and the illumination device may be embedded into the catheter. FIG. 18 shows an example distal portion of the catheter with integrated imaging device and the illumination device. A camera may be located at the distal portion. The distal tip may have a structure to receive the camera, illumination device and/or the location sensor. For example, the camera may be embedded into a cavity 1810 at the distal tip of the catheter. The cavity 1810 may be integrally formed with the distal portion of the cavity and may have a dimension matching a length/width of the camera such that the camera may not move relative to the catheter. The camera may be adjacent to the working channel 1820 of the catheter to provide near field view of the tissue or the organs. In some cases, the attitude or orientation of the imaging device may be controlled by controlling a rotational movement (e.g., roll) of the catheter.

The power to the camera may be provided by a wired cable. In some cases, the cable wire may be in a wire bundle providing power to the camera as well as illumination elements or other circuitry at the distal tip of the catheter. The camera and/or light source may be supplied with power from a power source located at the handle portion via wires, copper wires, or via any other suitable means running through the length of the catheter. In some cases, real-time images or video of the tissue or organ may be transmitted to an external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end of the endoscope, to the distal end of the robotic endoscope. In some embodiments of the disclosure, miniaturized LED lights may be employed and embedded into the distal portion of the catheter to reduce the design complexity. In some cases, the distal portion may comprise a structure 1430 having a dimension matching a dimension of the miniaturized LED light source. As shown in the illustrated example, two cavities 1430 may be integrally formed with the catheter to receive two LED light sources. For instance, the outer diameter of the distal tip may be around 4 to 4.4 millimeters (mm) and diameter of the working channel of the catheter may be around 2 mm such that two LED light sources may be embedded at the distal end. The outer diameter can be in any range smaller than 4 mm or greater than 4.4 mm, and the diameter of the working channel can be in any range according to the tool's dimensional or specific application. Any number of light sources may be included. The internal structure of the distal portion may be designed to fit any number of light sources.

In some cases, each of the LEDs may be connected to power wires which may run to the proximal handle. In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 1431 may be placed at the forwarding end face of the distal tip providing precise positioning of the LEDs as well as sufficient room for the glue. The cover 1831 may be composed of transparent material matching the refractive index of the glue so that the illumination light may not be obstructed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for controlling a robotic endoscope system, the method comprising:
   generating a 3D depth map of an environment surrounding the robotic endoscope system;
   autonomously actuating a self-propelled base of a robotic support system to a desired location relative to a patient bed based on the 3D depth map, wherein the robotic support system comprises a robotic arm coupled to the self-propelled base at a proximal end and an instrument driving mechanism (IDM) at a distal end; and
   actuating the robotic arm to autonomously align the IDM to a component coupled to or as a part of the patient bed.

2. The method of claim 1, wherein the 3D depth map is generated based at least in part on 3D point cloud data.

3. The method of claim 2, further comprising processing the 3D depth map to detect the patient bed and computing a position and orientation of the robotic support system relative to the patient bed.

4. The method of claim 1, wherein a flexible endoscope apparatus is releasably coupled to the IDM after the IDM is aligned to the component coupled to or as a part of the patient bed.

5. The method of claim 1, further comprising controlling a movement of the robotic arm to move the IDM to a predetermined distance from the component coupled to or as a part of the patient bed.

6. The method of claim 5, further comprising loading a flexible endoscope apparatus to be coupled to the IDM at a proximal end and coupled to the component at a distal end.

7. The method of claim 5, further comprising automatically adjusting a position of the IDM relative to the component upon detection of a buckling event.

8. The method of claim 1, further comprising detecting and recognizing an object in the environment and reconfiguring the robotic arm to avoid collision with the object while maintaining a position and orientation of the IDM.

9. The method of claim 8, further comprising detecting a buckling of a flexible catheter coupled to the IDM while the flexible catheter is inserted into a body of a patient.

10. The method of claim 9, further comprising executing a responsive velocity control algorithm to control a velocity of the tip of the flexible catheter while reconfiguring the robotic arm to avoid collision with the object.

11. The method of claim 1, wherein the IDM is autonomously aligned to the component based at least in part on sensor data.

12. The method of claim 11, wherein the sensor data is captured by electromagnetic sensors.

13. The method of claim 11, wherein the sensor data is captured by a camera including a fiducial marker placed on the component and wherein the 3D depth map comprises at least a 3D location of the fiducial marker.

14. A system for controlling a robotic endoscope system, the system comprising: a memory storing computer-executable instructions; one or more processors in communication with the robotic endoscope system and configured to execute the computer-executable instructions to:
   generate a 3D depth map of an environment surrounding the robotic endoscope system;
   autonomously actuate a self-propelled base of a robotic support system to a desired location relative to a patient bed based on the 3D depth map, wherein the robotic support system comprises a robotic arm coupled to the self-propelled base at a proximal end and an instrument driving mechanism (IDM) at a distal end; and
   actuate the robotic arm to autonomously align the IDM to a component coupled to or as a part of the patient bed.

15. The system of claim 14, wherein the 3D depth map is generated based at least in part on 3D point cloud data.

16. The system of claim 14, wherein the one or more processors are further configured to process the 3D depth map to detect the patient bed and compute a position and orientation of the robotic support system relative to the patient bed.

17. The system of claim 14, wherein a flexible endoscope apparatus is releasably coupled to the IDM after the IDM is aligned to the component coupled to or as a part of the patient bed.

18. The system of claim 14, wherein the one or more processors are further configured to control a movement of the robotic arm to move the IDM to a predetermined distance from the component coupled to or as a part of the patient bed.

19. The system of claim 18, wherein the one or more processors are further configured to load a flexible endoscope apparatus to be coupled to the IDM at a proximal end and coupled to the component at a distal end.

20. The system of claim 18, wherein the one or more processors are further configured to automatically adjust a position of the IDM relative to the component upon detection of a buckling event.

21. The system of claim 14, wherein the one or more processors are further configured to detect and recognize an object in the environment and reconfiguring the robotic arm to avoid collision with the object while maintaining a position and orientation of the IDM.

22. The system of claim 21, wherein the one or more processors are further configured to detect a buckling of a flexible catheter coupled to the IDM while the flexible catheter is inserted into a body of a patient.

23. The system of claim 22, wherein the one or more processors are further configured to execute a responsive velocity control algorithm to control a velocity of the tip of the flexible catheter while reconfiguring the robotic arm to avoid collision with the object.

24. The system of claim 14, wherein the IDM is autonomously aligned to the component based at least in part on sensor data.

25. The system of claim 14, wherein the sensor data is captured by electromagnetic sensors.

26. The system of claim 14, wherein the sensor data is captured by a camera including a fiducial marker placed on the component and wherein the 3D depth map comprises at least a 3D location of the fiducial marker.

* * * * *